United States Patent [19]

Hester, Jr. et al.

[11] Patent Number: 5,405,997
[45] Date of Patent: Apr. 11, 1995

[54] ANTIARRHYTHMIC METHANESULFONAMIDES

[75] Inventors: Jackson B. Hester, Jr., Galesbury; Salvatore C. Perricone, Delton; J. Kenneth Gibson, Kalamazoo, all of Mich.

[73] Assignee: The Upjohn Company, Kalamazoo, Mich.

[21] Appl. No.: 156,474

[22] Filed: Nov. 23, 1993

Related U.S. Application Data

[63] Continuation-in-part of Ser. No. 820,671, Jan. 17, 1992, abandoned, which is a continuation-in-part of Ser. No. 385,335, Jul. 25, 1989, abandoned.

[51] Int. Cl.⁶ .................... A61K 31/18; A61K 31/38; C07C 311/08; C07C 67/02
[52] U.S. Cl. ......................... 564/99; 560/251
[58] Field of Search .................. 564/99; 514/605, 821, 514/438; 560/251

[56] References Cited

U.S. PATENT DOCUMENTS

| | | | |
|---|---|---|---|
| 3,341,584 | 9/1967 | Larsen et al. | 260/556 |
| 3,478,149 | 11/1969 | Larsen et al. | 424/228 |
| 3,574,741 | 4/1971 | Gould et al. | 260/556 |
| 3,758,692 | 9/1973 | Larsen et al. | 424/321 |
| 4,507,320 | 3/1985 | DeMarinis et al. | 514/605 |
| 4,569,801 | 2/1986 | Molloy et al. | 260/501.21 |
| 4,596,827 | 6/1986 | Molloy et al. | 514/605 |
| 5,155,268 | 10/1992 | Kister, Jr. | 564/99 |

FOREIGN PATENT DOCUMENTS

| | | |
|---|---|---|
| 0134424 | 3/1985 | European Pat. Off. . |
| 0164865 | 12/1985 | European Pat. Off. . |
| 0304888 | 3/1989 | European Pat. Off. . |

OTHER PUBLICATIONS

Morgan, T. K., Jr. et al., "Synthesis and Class III Antiarrhythmic Activity of (Phenylbut-2-enyl)ammonium Salts. Effect of Conformation on Activity," J. Med. Chem. 29:1398-1405 (1986).

*Primary Examiner*—Peter O'Sullivan
*Attorney, Agent, or Firm*—D. L. Corneglio

[57] ABSTRACT

Methanesulfonamides are structurally depicted by Formula I'

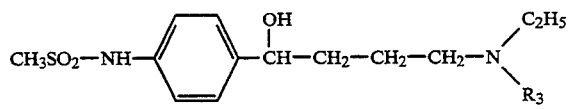

or its pharmacologically acceptable salts where $R_3$ is a $C_{1-7}$ alkyl substituted with $C_{3-7}$ cycloalkyl, or a $C_{1-10}$ alkyl substituted with one to eight fluorine atoms, one to three hydroxy, one to three $C_{1-5}$ acyloxy or one to three $C_{1-4}$ alkoxy substituents. These compounds are useful as Class III antiarrhythmic agents and are stable against rapid metabolism. Methods for treating cardiac arrhythmias with the compounds of Formula I' as well as compositions thereof are also described.

4 Claims, No Drawings

ANTIARRHYTHMIC METHANESULFONAMIDES

CROSS-REFERENCE TO RELATED PATENT APPLICATIONS

This application is a continuation-in-part of U.S. Ser. No. 07/820,671, filed Jan. 17, 1992, now abandoned, which was the national phase continuation of PCT/US90/03960, which was a continuation-in-part of U.S. Ser. No. 07/385,335, filed Jul. 25, 1989, abandoned.

BACKGROUND OF THE INVENTION

The present invention is directed toward compounds having a hydroxy-alkyl linkage between a tertiary amine group having a substituted side chain and a methanesulfonamide substituted phenyl, and preferably a terminal fluorine substitution. These novel methanesulfonamides prolong the effective refractory period of the myocardium and are very potent and stable against metabolism.

Antiarrhythmic drugs act upon the electrophysiological properties of the myocardium and conductive tissues. Typically the rhythmic contractions of the heart are dependent upon the ability of the myocardium and conductive tissues to respond to electrical impulses. When the conductivity of the heart's muscle and conductive tissue is altered by an occlusion of an artery or disease, a life threatening cardiovascular deterioration is likely. It is therefore desirable to treat the electrophysiological properties of the myocardium and conductive tissue to restore rhythmic contractions.

One means for restoring rhythmic contraction is with an antiarrhythmic agent that selectively prolongs the action potential duration and concomitantly increases the refractory period of heart cells without significant effect on cardiac conduction. Such drugs are classified as Class III antiarrhythmic agents. Class III antiarrhythmics which have good bioavailability and which do not affect other circulatory parameters such as blood pressure and heart rate are continually being sought. The subject compounds are Class III antiarrhythmics which are suitable for the treatment of mammals suffering from arrhythmic disorders or disease.

Bioavailability is an important characteristic of any drug. Unfortunately, with compounds similar to the subject compounds such as those disclosed in U.S. Pat. No. 5,155,268, bioavailability is hampered by a rapid metabolism of the amine side chain. Thus, the subject invention seeks to solve this problem by substituting the side chain to prevent rapid metabolism and thereby increase bioavailability. Surprisingly, these new compounds are more potent, too.

INFORMATION DISCLOSURE STATEMENT

The subject compounds are generally related to those compounds described in European Patent No. 0164865, which can be used as intermediates for the preparation of the subject compounds.

European Patent Application EP 0134424 discloses quaternary ammonium salts of compounds which are isomers of the subject alkanesulfonamides.

T. K. Morgan, Jr. et al., J. Med Chem., 29, 1398 (1986) reports tertiary amine alkanesulfonamides compounds.

U.S. Pat. Nos. 3,341,584 and 3,478,149 disclose sulfonamide compounds some of which can be used as intermediates for the preparation of the subject compounds.

Other U.S. Patents having examples of sulfonamide containing compounds and antiarrhythmic activity are DeMarinis et al. U.S. Pat. No. 4,507,320, Molloy et al. U.S. Pat. No. 4,569,801 and U.S. Pat. No. 4,596,827, and Gould et al. U.S. Pat. No. 3,574,741.

SUMMARY OF THE INVENTION

In one aspect the subject invention is directed toward a compound of Formula I', its enantiomers or pharmacologically acceptable salts thereof.

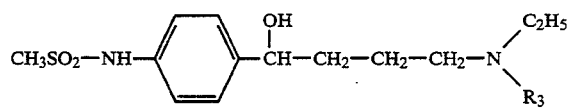

Formula I' is defined where $R_3$ is a $C_{1-7}$ alkyl substituted with $C_{3-7}$ cycloalkyl, or a $C_{1-10}$ alkyl, substituted with from one to eight fluorine atoms, or one to three hydroxy, one to three $C_{1-5}$ acyloxy or one to three $C_{1-4}$ alkoxy substituents.

In another aspect the subject invention is directed toward a method for treating cardiac arrhythmia in mammals comprising the administration of a therapeutically effective amount of a compound of Formula I' including pharmacologically acceptable salts thereof. An effective amount is from about 0.01 to about 300 mg. Preferably, the compound is administered in a unit dosage form for oral, sublingual, transdermal or parenteral administration.

The Formula I' compounds are generally prepared into pharmacological preparations or compositions for therapeutic administration to patients suffering from cardiac arrhythmia. The compounds are classified as Class III antiarrhythmic compounds which are agents that selectively prolong the action potential duration and concomitantly increase the refractory period of heart cells without significant effects on cardiac conduction.

DETAILED DESCRIPTION OF THE SUBJECT INVENTION

Alkanesulfonanilides which prolong the effective refractory period of the myocardium and are useful for treating cardiac arrhythmias in mammals are disclosed. The compounds of the present invention are represented by the structural Formula I', or its pharmaceutically acceptable salts. Formula I' is defined where $R_3$ is a $C_{1-7}$ alkyl substituted with a $C_{3-7}$ cycloalkyl, or a $C_{1-10}$ alkyl, substituted with from one to eight fluorine atoms, or one to three hydroxy, one to three $C_{1-5}$ acyloxy or one to three $C_{1-4}$ alkoxy substituents.

Typically, compounds similar to those described herein suffer from a bioavailability problem associated with rapid metabolism of the amine side chain (herein, $R_3$). It has been discovered that substitutions on this side chain can advantageously prevent rapid metabolism and thereby increase the therapeutic utility of the compounds.

An "alkyl" is a straight or branched carbon chain containing the number of carbon atoms designated such as $C_{1-4}$, $C_{1-5}$, $C_{1-10}$, etc. A "substituted" alkyl is a straight or branched carbon chain having a hydrogen atom replaced by another chemical group such as a cycloalkyl.

An "alkoxy" is an alcohol in which the hydrogen attached to the oxygen is replaced with a straight or branched carbon chain having one to four carbons.

A "cycloalkyl" is a cyclic ring structure formed from three to seven carbon atoms. The cyclic structure may also contain an alkyl substitution wherein the total carbons are calculated to include this substitution.

"Acyloxy" is an ester of a alcohol with a carboxylic acid having from one to five carbon atoms.

"Pharmacologically acceptable salts" are acid addition salts which can be prepared by any of the art recognized means. Typical, acid addition salts include hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates, fumarates and other pharmaceutically acceptable counter ions for amines.

The Formula I' compounds are used for the treatment of arrhythmia wherever a Class III antiarrhythmic drug is indicated. The compounds and compositions of Formula I' are administered in a therapeutic effective amount which is an amount sufficient to control arrhythmia in the host being treated such as mammals which includes humans. Typically, the Formula I' antiarrhythmic agents are used in unit dosages of from 0.01 to 300 mg in oral or injectable preparations. Preferably, the Formula I' compounds are used in unit dosages of 0.001 to 10 mg/kg for administration by routes either oral, sublingual, transdermal, or parenteral such as by subcutaneous, intramuscular, or intravenous injection.

The particular dose of compound administered according to this invention will of course be determined by the particular circumstances surrounding the case, including the compound administered, the route of administration, the particular arrhythmia being treated, and similar considerations.

The Formula I' compounds can be formulated into typical pharmaceutical preparations for either oral or parenteral administration. For example, the Formula I' compound can be formulated into a composition by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelation capsules for convenient oral administration.

A gelatin capsule suited to oral administration may contain, for example, a Formula I' compound in the amount of about 0.1 to about 100 mg. Such formulation can be administered orally as often as needed depending upon the particular condition and patient being treated.

For parenteral administration a Formula I' compound can be formulated for intramuscular or intravenous administration. In the case of treatment of a patient suffering from a severe cardiac arrhythmia, it may be desirable to administer the Formula I' compound by intravenous infusion in order to effect a speedy conversion to a normal cardiac rhythm. Such normal condition can then be maintained by oral administration.

The compositions of the present invention may also include sustained release oral dosage forms and controlled release dosage forms by which the effect of the dosage is through the skin. Such compositions are those known to an ordinary skilled artisan or can be ascertained by ordinary experimentation from known compositions such as creams, gels, pastes or liquids. Typical transdermal compounds are polyethylene glycol, triacetin, propylcarbonate, ethanol and isopropyl myristate.

The Formula I' compounds can be combined with other antiarrhythmic agents having the same or different mechanisms of action. For example, combinations may include, Class I antiarrhythmic agents, such as quinidine, tocainide, lidocaine or the like; Class II antiarrhythmic agents, such as, propranolol, sotalol, atenolol or the like; Class III antiarrhythmic agents such as clofilium, sotalol, amiodarone and meobentine; and Class IV antiarrhythmic agents such as verapamil or diltiazem.

Formula I compounds as shown in Examples 1–4, 6, 8, 10, 12, 14, 16 and 18 are prepared by dehydrating an appropriate benzylic alcohol.

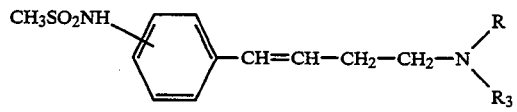

Examples of suitable starting materials are described in European Patents 0 164 865 and 0 233 051, U.S. Pat. Nos. 3,341,584, 3,478,149 all herein incorporated by reference. The dehydration procedure can be performed with trifluoroacetic acid in solvents such as chloroform or methylene chloride at temperatures of 0°–40° C. Olefins with an (E) configuration (trans) are generally the major products which are also the preferred products. Other intermediates useful in the preparation of the subject compounds are those alcohols not disclosed in the cited patents, where the corresponding $R_3$ group is a fluorinated alkyl, an alkenyl or an alkyl substituted by hydroxy, acyloxy or alkoxy or where $R_3$ is a $C_{1-7}$ alkyl substituted with an aryl, heteroaryl or $C_{3-7}$ cycloalkyl (Formula I'). Therefore these intermediates and their enantiomers are part of the subject invention.

The Formula I' compounds were evaluated for electrophysiological activity in an isolated, perfused rabbit cardiac tissue system. The method used was as follows:

New Zealand White rabbits of either sex (1.5–2.0 kg) were anesthetized and their hearts removed. The heart was immersed in ice cold perfusate while the right atria (RA), papillary muscles (PAP), and right ventricular muscle strips (RV) were isolated. The perfusate was continuously oxygenated with 95% oxygen and 5% carbon dioxide and contained the following in mM concentrations: NaCl 118.0; KCl 5.4; NaHCO$_3$ 25.0; MgCl$_2$ 1.2; KH$_2$PO$_4$ 1.0; CaCl$_2$ 2.4; glucose 110.0 and pyruvic acid 2.0. During hypoxic conditions the perfusate was exposed to a mixture of 83% nitrogen, 10% carbon dioxide and 7% oxygen. The pH during normoxia was approximately 7.4 and dropped to approximately 7.2 during hypoxic conditions.

The tissues were individually mounted on a plexiglass holder containing platinum stimulating electrodes and suspended in a 100 ml bath maintained at 30° C. by a circulating heat pump. All tissues were attached by silk suture to a force-displacement transducer and a tissue-dependent preload of 500–1000 mg was applied. RA were allowed to contract spontaneously. RV and PAP were stimulated at 2X threshold with 4 msec rectangular pulses at a frequency of 1 and 3 Hz. (Effective refractory period measurements percent increment over control are ERP1 and ERP3, conduction time measurements are CT1 and CT3). Between measurements those tissues were stimulated at a resting pace of 2 Hz. Each tissue served as its own baseline control and was allowed an equilibration period of two hours prior to experiments. During this period the perfusate was changed every 10–15 minutes.

Working solutions of the drugs were prepared by dissolving the drugs in distilled water and one drop of NaOH/ml to aid in dissolution (pH 9.4).

Measurements were made on each set of tissues after exposure to $10^{-7}$, $10^{-6}$, or $10^{-5}$M drug for 15 minutes; and $10^{-5}$M drug under hypoxic conditions for 15 minutes.

Automaticity (RATE), force of contraction (FOC) and threshold were measured directly on a polygraph. The ERP of cardiac tissues by definition is the longest coupling interval between the basic drive (S1) and the premature impulse (S2) that fails to propagate through the tissue. The S2 stimulus was introduced after every eighth S 1 which allowed time for stabilization of refractoriness. Refractory period measurements were made via a digital timing circuit. The limit of resolution for these refractory period measurements was approximately 6 msec. Conduction time measurements (CT) were recorded directly in msec by gently placing a teflon-coated silver bipolar electrode against the endocardial surface of the RV strip with the resulting electrocardiogram displayed on an oscilloscope. An increase in CT is equivalent to a decrease in conduction velocity.

Examples of Formula I' compounds evaluated in this manner are collected in Table I. A measure of the class III antiarrhythmic activity of these compounds is indicated by the percent increase in the effective refractory period of rabbit papillary muscle determined at pacing rates of 1 and 3 Hz ($ERP_1$ and $ERP_3$). The corresponding data for ibutilide, a compound of U.S. Pat. No. 5,155,268 is shown for comparison.

TABLE 1

| Example # | $R_3$ | $ERP_1$* | $(SE)^1$ | $ERP_3$** | $(SE)^1$ |
|---|---|---|---|---|---|
| 5 | (CH$_2$)$_5$CH(OH)CH$_3$ | 5.4 | (2.9) | 6.3 | (2.2) |
| 7 | (CH$_2$)$_2$CH(CH$_2$)$_5$ | 7.4 | (1.1) | 13.2 | (2.5) |
| 9 | CH$_2$CH$_2$CH(CH$_2$)$_4$ | 17.3 | (5.6) | 15.1 | (3.0) |
| 11 | (CH$_2$)$_3$C(CH$_3$)$_3$ | 6.0 | (3.9) | 8.8 | (4.2) |
| 13 | (CH$_2$)$_5$C(CH$_3$)$_2$OAc | 19.9 | (1.7) | 28.3 | (7.0) |
| 15 | (CH$_2$)$_5$C(CH$_3$)$_2$OH | 5.6 | (4.6) | 3.8 | (4.8) |
| 17 | (CH$_2$)$_5$C(CH$_3$)$_2$F | 16.2 | (5.6) | 24.3 | (3.0) |
| 19 | (CH$_2$)$_5$CF$_2$CH$_3$ | 22.8 | (8.7) | 18.6 | (11.9) |
| 20 | (CH$_2$)$_5$CH(F)CH$_3$ | 80.8 | (11.7) | 29.7 | (7.0) |
| 21 | (CH$_2$)$_5$CH(F)CH$_3$ | —[3] | —[3] | —[3] | —[3] |
| 22 | (CH$_2$)$_3$CH(CH$_2$)$_2$ | 17.9 | (1.8) | 21.2 | (6.4) |
| 23 | (CH$_2$)$_4$CH(CH$_2$)$_2$ | 22.8 | (1.2) | 20.5 | (6.1) |
| 24 | CH$_2$CH(CH$_2$)$_5$ | 34.8 | (8.6) | 16.3 | (18.9) |
| 25 | (CH$_2$)$_4$C(CH$_3$)$_2$OAc | 1.4 | (6.7) | 9.1 | (7.9) |
| 26 | (CH$_2$)$_4$C(CH$_3$)$_2$OH | 22.9 | (5.4) | 12.3 | (7.0) |
| 27 | (CH$_2$)$_4$C(CH$_3$)$_2$F | 18.2 | (11.6) | 14.2 | (8.9) |
| 28 | (CH$_2$)$_3$CH(CH$_2$)$_4$ | 16.6 | (3.9) | 13.9 | (1.8) |
| 29 | (CH$_2$)$_6$CHF$_2$ | 40.6 | (10.9) | 22.4 | (13.2) |
| 30 | (CH$_2$)$_5$CHF$_2$ | 34.6 | (12.5) | 5.3 | (5.4) |
| 31 | (CH$_2$)$_5$CH(CH$_2$)$_2$ | 25.7 | (6.4) | 30.6 | (15.6) |
| 32 | (CH$_2$)$_7$F | 21.6 | (7.2) | 21.6 | (7.1) |
| Ibutilide[2] | (CH$_2$)$_6$CH$_3$ | 18.0 | (4.1) | 15.8 | (2.0) |

*percent increase in the effective refractory period over control values measured at a drug concentration of $10^{-5}$M and a pacing rate of 1 Hz
**percent increase in the effective refractory period over control values measured at a drug concentration of $10^{-5}$M and a pacing rate of 3 Hz
[1] Standard error of the mean
[2] Not a compound of the invention
[3] Not tested

EXAMPLE 1

(E)-N-(4-(4-(Ethylheptylamino)-1-butenyl)phenyl)methanesulfonamide, (E)-2-butenedioate (2:1 salt (Formula Ia)

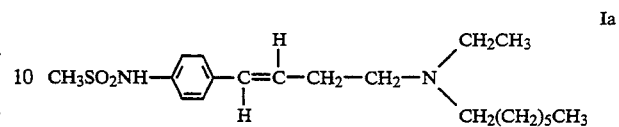

To a mixture of 1.75 ml of trifluoroacetic acid and 1.75 ml of CH$_2$Cl$_2$ at room temperature, under nitrogen, was added 0.63 g of N-(4-(4-(ethylheptylamino)-1-hydroxybutyl)phenyl)methanesulfonamide. The mixture was stirred for 24 hours at room temperature. The volatiles were allowed to evaporate under a stream of nitrogen and the residue partitioned between EtOAc and saturated NaHCO$_3$. The organic extracts were pooled and washed with brine. After drying (MgSO$_4$) the organic solution was concentrated in vacuo. The residue was flash chromatographed over 200 ml of silica gel; elution with 15% MeOH/CHCl$_3$ (8 ml fractions were taken). Fractions 26–42 were pooled and concentrated to give 0.36 g of clean product. The $^1$H NMR (300 MHz, CDCl$_3$) had: δ6.40 (d,1,J=16 Hz, ArCH=CH), 6.04 (p, 1, ArCH=CH). This material was combined with product isolated from two previous runs and partitioned between EtOAc and 8% aqueous NaHCO$_3$ to give 0.96 g (2.62 mmol) of the free base which was combined with 0.152 g (1.31 mmol) of fumaric acid in ethanol. The mixture was concentrated to a small volume and treated with Et$_2$O to the cloud point; cooling produced crystallization. Recrystallization from EtOH/Et$_2$O gave 0.75 of the hemifumarate, mp 112°–3°. The NMR, mass spectrum and IR were consistent with the proposed structure. Anal. calc'd for C$_{20}$H$_{34}$N$_2$O$_2$S·0.5 C$_4$H$_4$O$_4$: C, 62.23; H, 8.55; N, 6.60; S, 7.55. Found: C, 62.1; H, 8.72, N, 6.52; S, 7.41.

EXAMPLE 2

(E)-N-(4-(4-(Hexahydro-1H-azepin-1-yl)-1-butenyl)-phenyl)methanesulfonamide (E)-N-(4-(4-(Hexahydro-1H-azepin-1-yl)-1-butenyl)-phenyl)methanesulfonamide (2.0 g, 5.87 mmol) was dissolved in 7 ml of CH$_2$Cl$_2$, the mixture was cooled in an ice bath and treated dropwise with 7 ml of trifluoro acetic acid over 20 minutes. This mixture was stirred at room temperature for 48 hours and the volatiles were removed under a stream of N$_2$. The residue was diluted with EtOAc and washed twice with cold dilute NaHCO$_3$ and once water. The aqueous washes were combined and extracted with EtOAc. The organic extracts were combined, washed with brine, dried (MgSO$_4$) and concentrated to give 1.92 g of crude material. Chromatography over silica gel with 0.87 NH$_4$OH, 8.7 MeOH CH$_2$Cl$_2$ gave 0.73 g (38.6%) of product. The analytical sample was crystallized from Et$_2$O pentane, and had m.p. 73°–4° C. The IR, NMR and mass spectrum supported with the proposed structure. Anal calc'd for C$_{17}$H$_{26}$N$_2$O$_2$S: C, 63.32; H, 8.12; N, 8.69; S, 9.95. Found: C, 62.94; H, 8.00; N, 8.44; S, 9.95.

EXAMPLE 3

(E)-N-(4-(4-(Dibutylamino)-1-butenyl)phenyl)methanesulfonamide, (E)-2-Butenedioate (2:1 salt)

A solution of N-(4-(4-(dibutylamino)-1-hydroxybutyl)phenyl)methanesulfonamide, (2.08 g, 5.48 mmol) in 8 ml of $CH_2Cl_2$ was cooled in an ice bath and treated dropwise with 8 ml of $CF_3COOH$ over 10 minutes. This mixture was stirred at room temperature for 48 hours. The volatiles were removed under a stream of nitrogen; the residue was diluted with EtOAc and washed twice with cold, dilute $NaHCO_3$. The pooled aqueous wash was extracted with additional EtOAc. The pooled organic extract was washed with brine, dried ($MgSO_4$) and concentrated to give the crude product. Chromatography over silica gel with 0.87 $NH_4OH$ (8% MeOH/$CH_2Cl_2$ gave 1.11 g (49.3%) of product. The hemifumarate was prepared and crystallized from acetone to give 1.07 g, m.p. 131°–2° C. (softening at 124°). The IR, NMR and mass spectrum supported the proposed structure. Anal. calc'd for $C_{19}H_{32}N_2O_2S \cdot 0.5C_4H_4O_4$: C, 61.43; H, 8.35; N, 6.82; S, 7.81; Found: C, 61.44; H, 8.71; N, 6.53; S, 7.48.

EXAMPLE 4

In the process as described in Example 2 the starting alcohols listed in Table 2 are treated with trifluoroacetic acid to give the corresponding products listed in Table 3. The preparation of the starting alcohols (1–7) can be found in European Patent 0 164 865 and starting alcohol (8) can be found in European Patent 0 233 05 1.

Table 2

1) N-(4-(4-(Dipropylamino)-1-hydroxybutyl)phenyl-)isopropanesulfonamide
2) N-(4-(3-(Ethylheptylamino)-1-hydroxypropyl)-phenyl)methanesulfonamide
3) N-(4-(3-(Hexamethyleneimino)-1-hydroxypropyl)-phenyl)methanesulfonamide
4) N-(4-(3-(Dibutylamino)-1-hydroxypropyl)phenyl)-methanesulfonamide
5) N-(4-(4-(Heptamethyleneimino)-1-hydroxybutyl)-phenyl)methanesulfonamide
6) N-(3-(4-(Ethylheptylamino)-1-hydroxybutyl)-phenyl)methanesulfonamide
7) N-(4-(4-Decylethylamino)-1-hydroxybutyl)phenyl)-methanesulfonamide
8) N-(4-(1-hydroxy-3-(4-(4-pyridinyl)-1-piperazinyl)-propyl)phenyl)methanesulfonamide
9) N-(4-(4-(hexamethyleneimino)-1-hydroxypentyl)-phenyl)methane sulfonamide
10) N-(4-(4-(dibutylamino)-1-hydroxypentyl)phenyl)-methanesulfonamide Table 3

1) (E)-N-(4-(4-(Dipropylamino)1-butenyl)phenyl)isopropanesulfonamide
2) (E)-N-(4-(3-(Ethylheptylamino)-1-propenyl)phenyl)-methanesulfonamide
3) (E)-N-(4-(3-(Hexamethyleneimino)-1-propenyl)-phenyl)methanesulfonamide
4) (E)-N-(4-(3-(Dibutylamino)-1-propenyl)phenyl)methanesulfonamide
5) (E)-N-(4-(4-(Heptamethyleneimino)-1-butenyl)-phenyl)methanesulfonamide
6) (E)-N-(3-(4-(Ethylheptylamino)-1-butenyl)phenyl)-methanesulfonamide
7) (E)-N-(4-(4-(Decylethylamino)-1-butenyl)phenyl)-methanesulfonamide
8) (E)-N-(4-(3-(4-(4-pyridinyl)-1-piperazinyl)-1-propenyl)phenyl)methanesulfonamide
9) (E)-N-(4-(4-(Hexamethyleneimino)-1-pentenyl)-phenylmethanesulfonamide
10) (E)-N-(4-(4-(dibutylamino)-1-pentenyl)phenyl)methanesulfonamide.

EXAMPLE 5

N-(4-(4-(Ethyl(6-hydroxyheptyl)amino)-1-hydroxybutyl)phenyl)methanesulfonamide

Step I. A solution of 2-methylcyclohexanone (11.1 g, 0.099 mol) in chloroform (15 ml) was added during 20 minutes, under nitrogen, to a stirred suspension of m-chloroperbenzoic acid (24.6 g, 0.143 mol) in chloroform (250 ml). After 3 hours, 40 minutes, the mixture was poured into aqueous sodium bicarbonate and extracted with methylene chloride. The extract was washed with brine, dried ($MgSO_4$) and concentrated. The residue was distilled from a small amount of $K_2CO_3$ to give 9.58 g, bp 78°–79° C. (2.5–3 mm Hg) of 6-hydroxyheptanoic acid, ε-lactone.

Step II. A stirred suspension of dry ethylamine hydrochloride (3.26 g, 0.04 mol) in toluene, under nitrogen, was cooled in an ice bath and treated during 40 minutes with 20 ml of a 2.0M solution of trimethylaluminum in hexane. The mixture was kept at 0° for 10 minutes and at ambient temperature for 2.5 hours. A portion of the resulting solution (46.8 ml) was added, under nitrogen, during 15 minutes to a solution of the product from Step I (2.0 g, 0.016 mol) in toluene (100 ml). This mixture was warmed at 80° C. for 3 hours, cooled and added continuously to dilute HCl. The product was extracted with ethyl acetate. The extracts were dried ($MgSO_4$) and concentrated to give 2.27 g of N-ethyl-6-hydroxyheptanamide.

Step III. A stirred suspension of $LiAlH_4$ (2.65 g, 0.0697 mol) in THF (60 ml), under nitrogen, was cooled in an ice bath and treated during 20 minutes with a solution of the product from Step II (4.6 g, 0.0266 mol) in THF (60 ml). The mixture was warmed to ambient temperature during 30 minutes and then refluxed gently for 3.5 hours. It was again cooled in an ice bath and treated cautiously first with $H_2O$ (6 ml) and then with 2.5N NaOH (5.1 ml). This mixture was stirred at ambient temperature for 1 hour and filtered. The filtrate was concentrated and crystallized from hexane to give 2.63 g of ethyl(6-hydroxyheptyl)amine, mp 37°–38° C. The analytical sample had mp 39°–41° C. Anal. calc'd for $C_9H_{21}NO$: C, 67.87; H, 13.29; N, 8.80. Found: C, 67.69; H, 13.45; N, 8.81.

Step IV. A stirred solution of 4-((methanesulfonyl)amino)-γ-oxobenzenebutanoic acid (as described in EP 164 865) (0.49 g, 1.8 mmol) in THF (15 ml), under nitrogen, was treated with triethylamine (0.28 ml), cooled to −8° C. and treated during 5 minutes with isobutyl chloroformate (0.26 ml, 2.04 mmol). This mixture was kept at −5° to −8° C. for 90 minutes and then treated during 30 minutes with a solution of the product from Step III (0.31 g, 1.95 mmol) and triethyl amine (0.28 ml) in THF (10 ml). The mixture was kept at −8° C. for 2 hours and then poured into 1N HCl (19.2 ml). The product was extracted with EtOAc; the extract was washed successively with water, aqueous $NaHCO_3$, water and brine; dried ($MgSO_4$) and concentrated. The residue was crystallized frown EtOAc-hexane to give 0.36 g (48.6%) of N-ethyl-N-(6-hydroxyheptyl)-γ-oxo-4-((methanesulfonyl)amino)benzenebutanamide, mp 78°–80° C.

Step V. A solution of the product from Step IV (1.34 g, 3.28 mmol) in THF (25 ml) was added during 45 minutes under nitrogen, to an ice cold, stirred suspension of LiAlH$_4$ (0.31 g, 8.2 mmol) in THF (10 ml). The mixture was kept in the ice bath for 90 minutes and then treated cautiously with a solution of saturated aqueous sodium potassium tartrate (6.5 ml) and water (6.5 ml). The mixture was stirred for 90 minutes in the ice bath and then extracted with EtOAc. The extract was washed with brine, dried (MgSO$_4$) and concentrated; the residue was chromatographed over silica gel with 1% NH$_4$OH-10% MeOH—CHCl$_3$ to give 0.72 g of the titled product which is a compound of Formula I'. The high resolution FAB mass spectrum had (M+H)+ at m/z 401. Theory for C$_{20}$H$_{37}$N$_2$O$_4$S: 401.24; measured: 401.2480.

EXAMPLE 6

(E)-N-(4-(4-(Ethyl(6-hydroxyheptyl)amino)-1-butenyl)phenyl)methanesulfonamide

In the process as described in Example 2 the product of Example 5 is treated with trifluoroacetic acid to give the titled compound.

EXAMPLE 7

N-(4-(4-(Ethyl(2-cyclohexylethyl)amino)-1-hydroxybutyl)phenyl)methanesulfonamide Step I. A stirred suspension of 4-((methanesulfonyl)amino)-γ-oxobenzenebutanoic acid (described in EP 164 865) (20 g, 0.0737 mol) in THF (600 ml) was treated with 13.7 ml (0.098 ml) of triethylamine and cooled to −12° C. in an ice-methanol bath. This mixture was treated dropwise with isobutyl chloroformate (12.7 ml, 0.098 mol) and kept at −12° C. for 1.5 hours. A solution of ethylamine (4 g, 0.089 mol) and triethylamine (13.7 ml, 0.098 mol) in THF (173 ml) was then added dropwise. The mixture was kept at −12° C. for 3 hours and poured into 780 ml of ice-cold 1N HCl. Nitrogen was bubbled through this mixture to remove the THF. The solid was collected by filtration washed with aqueous NaHCO$_3$ and water and dried in vacuo to give 14.27 g of crude product. Additional product (4 g) was obtained by extracting the acid filtrate with EtOAc. The combined product was washed with MeOH and dried to give 13.75 g of N-ethyl-γ-oxo-4-((methanesulfonyl)amino)benzenebutanamide. The analytical sample was recrystallized from acetonitrile and had mp 210°–213° C. Anal. calc'd for C$_{13}$H$_{18}$N$_2$O$_4$S: C, 52.34; H, 6.08; N, 9.39; S, 10.75. Found: C, 52.02; H, 6.26; H, 9.28; S, 10.63.

Step II. The product from Step I (3.0 g, 0.010 mol) was added in small portions, under nitrogen to a stirred, ice-cold mixture of LiAlH$_4$ (1.15 g, 0.030 mol) in THF (75 ml). This mixture was kept in the ice bath for 1 hour and at ambient temperature for 2 hours. It was then mixed with an additional 100 ml of THF, refluxed for a few minutes and kept at ambient temperature for 18 hours. The mixture was treated carefully with 69 ml of a saturated sodium potassium tartrate solution and stirred for 1 hour. It was extracted with EtOAc. The extract was washed with a dilute sodium chloride solution. The aqueous layer contained the product; it was concentrated and finally freeze-dried. The resulting solid was extracted with MeOH. The methanol solution was concentrated and the residue extracted with CH$_2$Cl$_2$. The CH$_2$Cl$_2$ solution was concentrated to give 1.6 g of crude product that was purified by chromatography on silica gel with 1% NH$_4$OH-10 to 20% MeOH—CHCl$_3$. The product was crystallized from MeOH—EtOAc to give 540 mg of N-(4-(4-(ethylamino)-1-hydroxybutyl)phenyl)methanesulfonamide, mp 174°–176° C. The analytical sample was crystallized from MeOH and had mp 178.5°–180.5° C. Anal. calc'd for C$_{13}$H$_{22}$N$_2$O$_3$S: C, 54.52; H, 7.74; N, 9.78; S, 11.20. Found: C, 54.40; H, 7.84; N, 10.00; S, 11.02.

Step III. (Procedure E) A stirred solution of cyclohexylacetic acid (2.26 g, 0.0159 mol) and triethylamine (2.28 ml, 0.0163 ml) in THF (120 ml) was cooled to −8° C. and treated, dropwise, with isobutyl chloroformate (2.12 ml, 0.0163 ml). The mixture was kept at −8° C. for 1.5 hours and then treated with a mixture of the product from Step II (4.0 g, 0.014 mol) and triethylamine (2.28 ml, 0.0163 mol) in THF (160 ml). It was stirred at −8° C. for 2 hours, mixed with 1N HCl (158 ml) and extracted with EtOAc. The extract was washed with water and brine, dried (MgSO$_4$) and concentrated. The residue was chromatographed on silica gel with 2 to 6% MeOH—CHCl$_3$ to give 0.654 g of N-(4-(4-(ethylcyclohexylacetyl)amino)-1-hydroxybutyl)phenyl)methanesulfonamide. The mass spectrum had m/z 410 (M+).

Step IV. (Procedure C) A solution of 1M LiAlH$_4$ in THF (3.33 ml) was added, under nitrogen, to 3.33 ml of THF and the stirred solution was cooled in an ice bath and treated during 45 minutes with a solution of the product from Step III (654 mg, 0.00159 mol) in THF (6.42 ml). The mixture was kept in the ice bath for 1 hour 15 minutes and treated cautiously with a saturated aqueous solution of potassium sodium tartrate (3.37 ml). This mixture was extracted with EtOAc; the extract was washed with water and brine, dried (MgSO$_4$) and concentrated. The residue was chromatographed on silica gel with 3–10% MeOH—CHCl$_3$. A solution of the product in Et$_2$O was washed with NaHCO$_3$, dried (MgSO$_4$) and concentrated to give 185 mg of the titled compound, a compound of Formula I'. The high resolution mass spectrum of this compound had m/z 396 (M+). Theory for C$_{21}$H$_{36}$N$_2$O$_3$S: 396.2446; measured: 396.2451.

EXAMPLE 8

(E)-N-(4-(4-(Ethyl(2-cyclohexylethyl)amino)-1-butenyl)phenyl)methanesulfonamide

In the process as described in Example 2 the product of Example 7 is treated with trifluoroacetic acid to give the titled compound.

EXAMPLE 9

N-(4-(4-(Ethyl(2-cyclopentylethyl)amino)-1-hydroxybutyl)phenyl)methanesulfonamide Step I. A stirred solution of cyclopentylacetic acid (2 ml, 0.0159 mol) and triethylamine (2.28 ml, 0.0163 mol) in THF (120 ml) was cooled to −8° C. and treated, dropwise with isobutyl chloroformate (2.12 ml, 0.0163 mol). The mixture was kept at −8° C. for 1.5 hour and then treated with a mixture of the product from Example 7, Step II, (4.0 g, 0.014 mol) and triethylamine (2.28 ml, 0.0163 mol) in THF (160 ml). It was kept at −8° C. for 1.5 hour and then treated slowly with 1N HCl (158 ml). The product was extracted with EtOAc. The extract was washed successively with water, saturated aqueous NaHCO$_3$ and brine, dried (MgSO$_4$) and concentrated. The residue was chromatographed on silica gel with 5% MeOH—CH$_2$Cl$_2$ to give 3.0 g of N-(4-(4-(ethyl(cyclopentylacetyl)amino)-1-hydroxybutyl)-phenyl)methanesulfonamide. The mass spectrum had m/z 396 (M+).

Step II. A 1M solution of LiAlH$_4$ in THF (15.9 ml) was mixed with THF (15.9 ml) and cooled, under nitrogen in an ice bath. To this solution was added, dropwise, with stirring, a solution of the product from Step I (3.0 g, 0.0076 mol) in THF (30.7 ml). The mixture was kept in the ice bath for 1 hour and then treated cautiously with a saturated potassium sodium tartrate solution (16.1 ml). This mixture was stirred at ambient temperature for 45 minutes and extracted with EtOAc. The extract was washed with water, dried (MgSO$_4$) and concentrated. The residue was chromatographed on silica gel with 10–20% MeOH—CHCl$_3$. A solution of the product in Et$_2$O was washed with NaHCO$_3$ and concentrated to give 1.86 g of the titled compound which is a compound of Formula I'. The mass spectrum had m/z 382 (M+). Theory for C$_{20}$H$_{34}$N$_2$O$_3$S: 382.2290; measured: 382.2291.

EXAMPLE 10

(E)-N-(4-(4-(Ethyl(2-cyclopentylethyl)amino)-1-butenyl)phenyl)methanesulfonamide In the process as described in Example 2 the product of Example 9 is treated with trifluoroacetic acid to give the titled compound.

EXAMPLE 11

N-(4-(4-(Ethyl(4,4-dimethylpentyl)amino)-1-hydroxybutyl)phenyl)methanesulfonamide (Intermediate for Example 12)

Step I. A stirred solution of 4,4-dimethylpentanoic acid (2.07 g, 0.0159 mol) and triethylamine (2.28 ml, 0.0163 mol) in THF (120 ml) was cooled to −8° C. and treated dropwise with isobutyl chloroformate (2.12 ml, 0.0163 mol). The mixture was kept at −8° C. for 1.5 hour and treated with a mixture of the product from Example 7 Step II (4.0 g, 0.014 mol), triethylamine (2.28 ml, 0.0163 mol) and THF (160 ml). This mixture was kept at −8° C. for 1.5 hour and then treated slowly with 1N HCl (158 ml) and extracted with EtOAc. The extract was washed with water, dilute NaHCO$_3$ and water, dried (MgSO$_4$) and concentrated to give 4.4 g of N-(4-(4-(ethyl(4,4-dimethylpentanoyl)amino)-1-hydroxybutyl)-phenyl)methanesulfonamide. The mass spectrum had m/z 398 (M+).

Step II. A solution of the product from Step I (4.4 g, 0.0115 mol) in THF (46.4 ml) was added dropwise during 45 minutes, under nitrogen to a stirred, ice cold mixture of a 1M solution of LiAlH$_4$ in THF (24.0 ml) and THF (24 ml). The mixture was kept in the ice bath for 45 minutes and then treated slowly with a saturated aqueous solution of potassium sodium tartrate (24.4 ml). This mixture was stirred for 30 minutes and extracted with EtOAc. The extracts were washed with water and brine, dried (MgSO$_4$) and concentrated. The residue was chromatographed on silica gel with 5–10% MeOH—CHCl$_3$. The product was dissolved in Et$_2$O, washed with NaHCO$_3$, dried (MgSO$_4$) and concentrated to give 2.96 of the titled compound. The FAB mass spectrum had m/z 385 (M+H)+. Theory for C$_{20}$H$_{37}$N$_2$O$_3$S: 385.2525; measured.: 385.2546.

EXAMPLE 12

(E)-N-(4-(4-(Ethyl(4,4-dimethylpentyl)amino)-1-butenyl)phenyl)methanesulfonamide In the process as described in Example 2 the product of Example 11 is treated with trifluoroacetic acid to give the titled compound.

EXAMPLE 13

N-(4-(4-(Ethyl(6-acetoxy-6-methylheptyl)amino)-1-hydroxybutyl)phenyl)methanesulfonamide Step I. A stirred solution of pentamethylene chlorohydrin (10.0 g, 0.0816 mol) in Et$_2$O (165 ml) under nitrogen was treated with 3,4-dihydro-2H-pyran (10.3 g, 0.122 mol) and p-toluenesulfonic acid hydrate (0.5 g) and kept at ambient temperature for 4.5 hours. The mixture was washed with aqueous NaHCO$_3$ and brine, dried (MgSO$_4$) and concentrated. The residue was distilled to give 4.06 g, bp 79°–82° C. (0.1–0.07 mm Hg) and 10.54 g, bp 82°–84° C. (0.1–0.07 mm Hg) of 5-chloropentyl 2-tetrahydropyranyl ether.

Step II. A small portion of a solution of the product from Step I (21.1 g, 0.102 mol) in THF (105 ml) was added, under nitrogen, to magnesium turnings (5.0 g, 0.204 g-atom). The mixture was warmed in an oil bath at 75°–80° and the reaction was started by the addition of 1.5 ml of a 1M solution of 1,2-dibromoethane in THF. The remaining chloroalkane solution was then added during 20 minutes. The resulting mixture was refluxed for 45 minutes, cooled in an ice bath and treated during 15 minutes with a solution of acetone (9.0 ml, 0.123 mol) in THF (95 ml). It was kept at ambient temperature for 16 hours, cooled in an ice bath and treated during 15 minutes with saturated aqueous NH$_4$Cl (115 ml). The resulting mixture was extracted with EtO. The extract was washed with water and brine, dried (MgSO$_4$) and concentrated to give 30.5 g of crude product. Distillation gave 16.77 g of 6-hydroxy-6-methylheptyl 2-tetrahydropyranyl ether, bp 107°–115° (0.07–0.1 mm Hg). The CI mass spectrum had m/z 231 (M+H)+.

Step III. A solution of the product from Step II (5.0 g, 0.0217 mol) in triethylamine (6.1 ml, 0.0434 mol), under nitrogen, was treated with acetic anhydride (4.1 ml, 0.434 mol) and 4-dimethylaminopyridine (0.27 g, 0.00217 mol). It was kept at ambient temperature for 20.5 hours, diluted with hexane (100 ml), washed successively with 75 ml of cold 5% HCl, aqueous NaHCO$_3$ and brine, dried (MgSO$_4$) and concentrated. The residue was chromatographed on silica gel with 0.05% Et$_3$N-5% EtOAc-hexane to give 4.92 g of 6-acetoxy-6-methylheptyl 2-tetrahydranyl ether. The CI mass spectrum had m/z 273 (M+H)+.

Step IV. A stirred solution of the product from Step III (4.83 g, 0.0177 mol) in absolute EtOH (150 ml) was treated with pyridinium p-toluenesulfonate (0.58 g, 0.0023 mol), kept at ambient temperature for 46 hours and concentrated. The residue was dissolved in Et$_2$O, washed with aqueous NaHCO$_3$ and brine, dried (MgSO$_4$) and concentrated. The resulting oil was chromatographed on silica gel with 0.05% Et$_3$N-5 to 20% EtOAc-hexane to give 2.88 g of 6-acetox-6-methyl-1-heptanol.

Step V. A stirred solution of the product from Step IV (2.79 g, 0.0148 mol) in benzene (27 ml), under nitrogen, was treated with triphenylphosphine (4.27 g, 0.0163 mol), cooled in an ice bath and treated, portion wise during 26 minutes, with N-bromosuccinimide (2.90 g, 0.0163 mol). The mixture was kept in the ice bath for 30 minutes and at ambient temperature for 4.5 hours. It was then mixed with pentane (100 ml). The solid was collected by filtration and washed with pentane. The filtrate was concentrated; the residue was again mixed with pentane and filtered. This filtrate was mixed with a little Et$_2$O, washed successively with cold 5% aqueous sodium thiosulfate, 0.5N NaOH and brine, dried (MgSO$_4$) and concentrated. The residue was chromatographed on silica gel with 1.5–2% EtOAc-hexane to give 3.25 g of 6-acetoxy-1-bromo-6-methylheptane.

Step VI. A stirred mixture of the product from Example 7, Step II (1.5 g, 0.00524 mol), the product from Step V above 1.45 g, 0.00576 mol), sodium bicarbonate (0.88 g, 0.0105 mol) and acetonitrile (45 ml) was warmed at 90°–95°, under nitrogen for 6 hours and kept at ambient temperature for 11 hours. It was then filtered. The filtrate was concentrated and the residue chromatographed on silica gel with 0.5% NH$_4$OH-6% MeOH—CH$_2$Cl$_2$ to give 1.63 g of the titled compound which is a compound of Formula I'. The high resolution mass spectrum had m/z 456 (M+). Theory for C$_{23}$H$_{40}$N$_2$O$_5$S: 456.2658; measured: 456.2650.

EXAMPLE 14

(E)-N-(4-(4-(Ethyl(6-acetoxy-6-methylheptyl)amino)-1-butenyl)phenyl)methanesulfonamide In the process as described in Example 2 the product from Example 13 is treated with trifluoroacetic acid to give the titled compound.

EXAMPLE 15

N-(4-(4-(Ethyl(6-hydroxy-6-methylheptyl)amino)-1-hydroxybutyl)phenyl)methanesulfonamide A stirred solution of the product from Example 13 (1.35 g, 0.00296 mol) in methanol (80 ml) was treated with a solution of K$_2$CO$_3$ (2.04 g, 0.0148 mol) in water (5.9 ml) and the mixture was refluxed for 21.5 hours. It was kept at ambient temperature for 42.5 hours and concentrated to an aqueous residue which was mixed with water (10 ml) and CH$_2$Cl$_2$, acidified to pH 8.5–9 with 6 NHCl, saturated with NaCl and extracted with CH$_2$Cl$_2$. The extract was dried (MgSO$_4$), concentrated and the residue chromatographed on silica gel with 0.5% NH$_4$OH-9% MeOH—CH$_2$Cl$_2$ to give 1.1 g of the titled compound which is a compound of Formula I'. The high resolution mass spectrum had m/z 414(M+). Theory for C$_{21}$H$_{38}$N$_2$O$_4$S: 414.2552; measured: 414.2560.

EXAMPLE 16

(E)-N-(4-(4-(Ethyl(6-hydroxy-6-methylheptyl)amino)-1-butenyl)phenyl)methanesulfonamide In the process as described in Example 2 the product from Example 15 is treated with trifluoroacetic acid to give the titled compound which is a compound of Formula I.

EXAMPLE 17

N-(4-(4-(Ethyl(6-fluoro-6-methylheptyl)amino)-1-hydroxybutyl)phenyl)methanesulfonamide Step I. A solution of the product from Example 13, Step II, (3.97 g, 0.0173 mol) in CH$_2$Cl$_2$ (12 ml) was added under nitrogen, during 4.5 minutes to a stirred solution of diethylaminosulfur trifluoride (4.6 ml, 0.0345 mol) in CH$_2$Cl$_2$ (12 ml) that had been cooled in a dry ice acetone bath (−78° C.). The mixture was kept: in the bath for 15 minutes, warmed to 0° during 10 minutes and mixed with 10% aqueous Na$_2$CO$_3$ (60 ml). This mixture was extracted with CH$_2$Cl$_2$. The extracts were washed with water, dried (MgSO$_4$) and concentrated. The residue was chromatographed on silica gel with 0.05% Et$_3$N-2.5% EtOAc-hexane to give 3.36 g of 6-fluoro-6-methylheptyl-2-tetrahydropyranyl ether.

Step II. A stirred solution of the product from Step I (3.34 g, 0.0144 mol) in absolute EtOH was treated with pyridinium p-toluenesulfonate (0.47 g, 0.00187 mol) and kept under nitrogen at ambient temperature for 41 hours. The mixture was concentrated and the residue, dissolved in EtOAc, was washed with aqueous NaHCO$_3$ and brine, dried (MgSO$_4$) and concentrated. The residue was chromatographed on silica gel with 5 to 20% EtOAc-hexane to give 1.86 g of 6-fluoro-6-methyl-1-heptanol.

Step III. A stirred solution of the product from Step II (0.427 g, 0.00288 mol) in benzene (5.2 ml) was mixed with triphenylphosphine (0.83 g, 0400317 mol) cooled in an ice bath and treated, portion-wise, during 26 minutes with N-bromosuccinimide (0.56 g, 0.00317 mol). The mixture was kept in the ice bath for 30 minutes and at ambient temperature for 3.5 hours; it was then diluted with pentane (20 ml), cooled in an ice bath for a few minutes and filtered. The solid was washed with pentane and the filtrate was concentrated. A mixture of the residue and pentane was cooled in an ice bath for a few minutes and again filtered. The filtrate was mixed with Et$_2$O and washed successively with cold 5% aqueous sodium thiosulfate, 0.5N NaOH and brine, dried (MgSO$_4$) and concentrated. The residue was chromatographed on silica gel with 1–3% EtOAc-hexane to give 0.440 g of 1-bromo-6-fluoro-6-methylheptane.

Step IV. (Procedure B) A stirred mixture of the product from Example 7, Step II, (0.37 g, 0.00128 mol), the product from Step III above (0.298 g, 0.0141 mol), sodium bicarbonate (0.21 g, 0.0026 mol) and acetonitrile (11 ml) was refluxed for 5 hours and kept at ambient temperature for 18 hours. It was filtered and the solid was washed with acetonitrile. The filtrate was concentrated and the residue was chromatographed on silica gel with 10% MeOH—CH$_2$Cl$_2$ to give 0.332 g of the titled product, a compound of Formula I'. The mass spectrum had m/z 416 (M+).

EXAMPLE 18

(E)-N-(4-(4-(Ethyl(6-fluoro-6-methylheptyl)amino)-1-butenyl)phenyl)methanesulfonamide In the process as described in Example 2 the product from Example 17 is treated with trifluoroacetic acid to give the titled compound.

EXAMPLE 19

N-[4-[4-[(6,6-Difluoroheptyl)ethylamino]-1-hydroxybutyl]phenyl]-methanesulfonamide Step I. To a N$_2$ covered solution of 1.0 g (6.94 mmol) of 5-acetylvaleric acid in 50 mL of THF was added 1.29 mL (9.23 mmol) of triethylamine. After stirring for 5 min at room temperature the solution was cooled in an ice-isopropanol bath (−5° to −10° C.) and there was added, dropwise over 2 min, 1.2 mL (9.23 mmol) of isobutyl chloroformate. A resulting thick suspension was stirred in the cold for 3 h and there was then added over 8.5 min a solution of 0.7 mL (10.4 mmol) of ethyl amine and 1.29 mL (9.23 mmol) of triethylamine in 15 mL of THF. After stirring in the cold for an additional 2.75 h the reaction mixture was allowed to warm partially and a suspended solid was removed by filtration and washed well with Et₂O. The combined filtrates were concentrated in vacuo and the residue chromatographed over silica gel (3% MeOH:CH₂Cl₂). The crystalline residue was recrystallized from Et₂O to yield 0.338 g, mp 55.5°–58° C.; 0.27 g, mp 55°–57.5° C. and 0.073 g, mp 53.5°–56° C. of the amide. The analytical sample had: mp 55.5°–58° C.; NMR (CDCl₃) δ1.15 (t, 3H), 1.61 (m, 4H), 2.15 (s, 3H), 2.18 (m, 2H), 2.48 (m, 2H), 3.30 (m, 2H), 5.67 (broad s, 1H). Anal. calc'd for C₉H₁₇N₁: C, 63.13; H, 10.01; N, 8.18. Found: C, 63.08; H, 10.22; N, 8.05.

Step II. According to the method of Sondej and Katzenellenbogen a N₂ covered mixture of 0.5 g (2.92 mmol) of the product from Step I and 0.49 mL (5.84 mmol) of 1,2 ethanedithiol was treated with 0.41 mL (2.9 mmol) of boron trifluoride-acetic acid complex. After stirring the resulting solution vigorously at room temperature for 15 min the reaction mixture was diluted with 10 mL of EtOAc and washed once with 10 mL of aqueous NaHCO₃, once with 10 mL of 15% NaOH and once with brine, dried over MgSO₄ and concentrated in vacuo. The crystalline residue was chromatographed over silica gel (1.5% MeOH: 0.05% Et₃N:CH₂Cl₂) and recrystallized from Et₂O:pentane to yield a 0.313 g, mp 54°–55° C.; 0.1941 g mp 53.5°–55° C. and 0.0903 g mp 53°–54.5° C. of product. The analytical sample had: mp 54°–55° C.; NMR (CDCl₃) δ1.14 (t, 3H), 1.54 (m, 2H), 1.68 (m, 2H), 1.75 (s, 3H), 1.95 (m, 2H), 2.18 (m, 2H), 3.31 (m, 6H), 5.46 (broad s, 1H); MS (relative intensity) 247 (M⁺, 22.5), 214 (10.5), 203 (2.1), 188 (40.0), 154 (50.1), 119 (100), 87 (47.4); IR (Nujol) 3300, 3206, 3098, 1641 cm⁻¹. Anal. calc'd. for C₁₁H₂₁N₁O₁S₂: C, 53.40; H, 8.56; N, 5.66; S, 25.92. Found: C, 53.62; H, 8.55; N, 5.64; S, 25.78.

Step III. According to the method of Sondej and Katzenellenbogen a N₂ covered, dry ice:Me₂CO cooled suspension of 0.116 g (0.404 mmol) of 1.3-dibromo-5,5-dimethylhydantoin in 0.8 mL of CH₂Cl₂ was treated with 0.2 mL of hydrogen fluoride-pyridine followed by a solution of 0.10 g (0.404 mmol) of the product from Step II in 0.2 mL of CH₂Cl₂. After stirring in the cold for 10 min and then at room temperature for 15 min the reaction mixture was pipetted onto 3 mL basic alumina column (contained in a plastic disposable syringe barrel) and eluted with CH₂Cl₂. The eluate containing product(s) was concentrated in vacuo. The residue was chromatographed over silica gel (1% MOH:CH₂Cl₂ followed by 2% MeOH:CH₂Cl₂) to yield 0.0205 g of crystalline product; mp 41°–42° C.; NMR (CDCl₃) δ1.14 (t, 3H), 1.52 (m, 2H), 1.58 (t, 3H, J=30.7 Hz), 1.67 (m, 2H), 1.85 (m, 2H), 2.19 (t, 2H), 3.30 (m, 2H), 5.51 (broad s); MS m/z (relative intensity) 193 (M⁺, 1.9), 178 (4.5), 149 (3.4), 129 (6.2), 114 (6.6), 100 (9.9), 87 (100).

Step IV. A stirred suspension of LiAlH₄ (0.21 g, 5.65 mmol) in THF (5 mL) was cooled in an ice bath, under N₂, and treated, dropwise during 4.5 rain, with a solution of the product from Step III, 0.464 g, 2.4 mmol) in THF (5 mL). The mixture was kept in the ice bath for 10 min, at ambient temperature for 1 h and at 80° for 2.5 h. It was then cooled in an ice bath and treated successively with water (0.2 mL), 15% NaOH (0.2 mL) and water (0.6 mL). This mixture was stirred at ambient temperature for 1 h and filtered through Celite. The filtrate was concentrated to give 0.450 g of an oily residue which was chromatographed on silica gel, with 5% MeOH/0.5% NH₄OH CH₂Cl₂ to give 0.336 g (6,6-difluoroheptyl)ethylamine: NMR (CDCl₃) δ1.12 (t, 3H), 1.5 (m, 7H), 1.58 (t, 3H, J=30.7 Hz), 1.84 (m, 2H), 2.65 (m, 4H).

Step V. Triethylamine (0.33 mL, 2.38 mmol) was added, under nitrogen, to a stirred suspension of 4-((methanesulfonyl)amino)-α-oxobenzoic acid (as described in EP 164865) (0.56 g, 2.06 mmol) in THF (10 mL). After 30 min the solution was cooled in an ice-MeOH bath and treated with isobutyl chloroformate (0.31 mL, 2.38 mmol); a solid precipitated. This mixture was kept in the bath for 2 h and then treated with the product from Step IV (0.336 g, 1.87 mmol), triethylamine (0.33 mL, 2.38 mmol) and THF (0.7 mL). Stirring in a cold bath was continued for 21 h. The mixture was then filtered through Celite and the solid was washed with EtOAc. The filtrate was concentrated and the residue (1.419 g) was chromatographed on silica gel with 2% MeOH/CH₂Cl₂. The product thus obtained mounted to 0.379 g: mp 103°–108° C.; NMR (CDCl₃) δ1.48 (broad m, 14H), 2.82 (m, 2H), 3.01 (s, 3H), 3.27 (m, 2H), 3.42 (m. 4H), 7.21 (d, 2H), 7.81 (d, 2H), 8.61 (d, 1H); MS m/z (relative intensity) 432(M⁺, 9.3), 254 (100), 234 (28.0), 198 (32.8), 178 (49.2), 119 (14.3).

Step VI. A stirred suspension of LiAlH₄ (0.11 g, 2.89 mmol) in THF (2 mL) was cooled, under nitrogen, in an ice bath and treated, dropwise during 9 min, with a solution of the product from Step V (0.379 g, 0.877 mol) in THF (5 mL). The mixture was kept in the bath for 2.5 h and then treated carefully, dropwise during 4 min, with a saturated aqueous solution of potassium sodium tartrate (1.4 mL). This mixture was stirred for 20 min and filtered through Celite. The solid was washed first with EtOAc and then with CH₂Cl₂. The filtrates were concentrated and the combined residue was chromatographed on silica gel with 5% MeOH/0.5% NH₄OH/CH₂Cl₂ to give 0.228 g of the titled product, an oil which is a compound of Formula I'. The high resolution mass spectrum had m/z 420(M⁺). Theory for C₂₀H₃₄F₂N₂O₃S: 420.2258; measured: 420.2265.

EXAMPLE 20

N-[4-[4-[(6-Fluoroheptyl)ethylamino]-1-hydroxybutyl]-phenyl]methanesulfonamide

Step I. To a N₂ covered, mechanically stirred solution of 0.5 g (3.14 mmol) of the product from Example 5, Step III in 2.4 mL of H₂O was added 0.67 g (6.28 mmol) of sodium carbonate. After cooling in an ice bath, there was added dropwise over 20 min a solution of 0.45 mL (3.14 mmol) of benzyl chloroformate in 6 mL of CH₂Cl₂. After stirring in the cold for 1.5 h the ice bath was allowed to warm and the mixture was kept at room temperature for 20 h. There was then added 2.5 mL of H₂O and the two phased mixture was stirred until it became clear. The aqueous layer was washed twice with CH₂Cl₂ and the combined organic fractions were dried over MgSO₄ and concentrated in vacuo. The residue was chromatographed over silica gel (1.25% MeOH:CH₂Cl₂) to yield 0.772 g (83.8%) of the CBZ protected amine; NMR (CDCl₃) δ1.14 (m, 6H), 1.4 (m, 8H), 1.91 (s, 1H), 3.26 (m, 4H), 3.75 (m, 1H), 5.13 (s, 2H), 7.35 (m, 4H); MS m/z (relative intensity) 293 (M⁺, 2.2), 275 (1.3), 158 (40.0), 91 (100); IR (Nujol) 3455, 1700 cm⁻¹.

Step II. To a dry ice:Me₂CO cooled solution of 0.7 mL (5.26 mmol) of diethylaminosulfuryl fluoride in 2 mL of $CH_2Cl_2$, under nitrogen was added over 9 min a solution of 0.772 g (2.63 mmol) of the product from Step I in 2 mL of $CH_2Cl_2$. After stirring in the dry ice:$Me_2CO$ bath for 15 min and then in an ice bath for 20 min the reaction mixture was pipetted over 2 min into 9.5 mL of well stirred 10% aqueous $Na_2CO_3$. After stirring for an additional 2 min the aqueous layer was separated and washed twice with $CH_2Cl_2$. The combined organic fractions were dried over $MgSO_4$ and concentrated in vacuo. The residue was chromatographed over silica gel (7.5% EtOAc:hexane) to yield 0.5576 g (71.5%) of the fluorinated product; NMR ($CDCl_3$) δ1.11 (m, 3H), 1.4 (m, 11H), 3.25 (m, 4H), 4.53, 4.7 (m's, 1H), 5.13 (s, 2H), 7.35 (m, 4H); MS m/z (relative intensity) 295 ($M^+$, 42.8), 148 (100).

Step III. To a $N_2$ covered solution of 0.557 g (1.89 mmol) of the product from Step II in 6 mL of MeOH was added 0.357 g (5.66 mmol) of ammonium formate followed by 0.35 g of 10% Pd/C. After stirring for 25 min the catalyst was removed by filtration through Celite and the filtrate was concentrated in vacuo. The residue was chromatographed over silica gel (5% MeOH:0.5% $NH_4OH:CH_2Cl_2$ followed by 7.5% MeOH:0.5% $NH_4OH:CH_2Cl_2$). The product containing fractions were concentrated in vacuo. A solution of the residue in EtOAc was washed once with aqueous $NaHCO_3$, dried over $MgSO_4$ and concentrated in vacuo to yield 0.231 g (75.8%)of (6-fluoroheptyl)ethylamine: NMR ($CDCl_3$) δ1.11 (t, 3H), 1.45 (m, 12H), 2.64 (m, 4H), 4.57, 4.72 (m's, 1H).

Step IV. A stirred suspension of 4-((methanesulfonyl)amino)-α-oxobenzoic acid (as described in EP 164865 (0.388 g, 1.43 mmol) in THF (7 mL), under nitrogen, was treated with triethylamine (0.23 mL, 1.66 mmol) and kept at ambient temperature for 20 min. The solution was then cooled in an ice-MeOH bath and treated, dropwise during 1 min, with isobutyl chloroformate (0.22 mL, 1.66 mmol). This mixture was kept in the bath for 2 h and treated dropwise during 3 min, with a solution of the product from Step III (0.231 g, 1.43 mmol) and triethylamine (0.23 mL, 1.66 mmol) in THF (0.5 mL); it was kept at −2° C. for 19 h and filtered through Celite. The solid was washed with EtOAc and the combined filtrate was concentrated in vacuo. The residue was chromatographed on silica gel with 2% MeOH—$CH_2Cl_2$ to give 0.270 g of N-[4-[4-[Ethyl(6-fluoroheptyl)amino]-1,4-dioxobutyl]phenyl]methanesulfonamide: NMR ($CDCl_3$) δ1.45 (m, 14H), 2.81 (m, 2H), 3.02 (s, 3H), 3.37 (m, 6H), 4.55, 4.72 (m's, 1H), 7.20 (d, 2H), 7.83 (d, 2H), 8.4 (d, 1H); FABMS m/z (relative intensity) 415 ($M+H^+$, 22.8), 337 (1.95), 254 (100), 216 (4.7), 198 (22.0), 162 (18.7), 55 (64.4).

Step V. (Procedure A) A stirred suspension of $LiAlH_4$ (0.089 g, 2.34 mmol) in THF (1.5 mL) was cooled, under nitrogen, in an ice bath and treated, dropwise during 9 min, with a solution of the product from Step IV (0.270 g, 0.706 mmol) in THF (4 mL). The mixture was kept in the bath for 2 h 20 min and then treated, dropwise, cautiously with saturated aqueous potassium sodium tartrate (3.0 mL). This mixture was stirred for 25 min and then extracted with EtOAc. The aqueous layer was filtered through Celite and the solid and aqueous filtrate were both extracted with EtOAc. The combined EtOAc extracts were washed with brine, dried ($MgSO_4$) and concentrated in vacuo to give a gummy residue (0.232 g) which was chromatographed in silica gel with 5% MeOH/0.5% $NH_4OH/CH_2Cl_2$ to give 0.217 g (76.3%) of the titled product, a compound of Formula I': NMR ($CDCl_3$) δ1.09 (t, 3H), 1.5 (m, 14H), 1.95 (m, 1H), 2.55 (m, 6H), 2.93 (s, 3H), 4.60, 4.73 (m's, 1H), 4.61 (m, 1H), 7.15 (d, 2H), 7.35 (d, 2H); MS m/z (relative intensity)402 ($M^+$, 11.4), 323 (32.1), 299 (47.2), 174 (100); high resolution mass spectrum theory for $C_{20}H_{35}FN_2O_3S$: 402.2352; measured: 402.2347.

EXAMPLE 21

N-(4-(4-((6-Fluoroheptyl)ethylamino)-1-hydroxybutyl)-phenyl)methanesulfonamide, (E)-2-butenedioate (2:1 salt).

A sample of N-[4-[4-[(6-fluoroheptyl)ethylamino]-1-hydroxybutyl]phenyl]methanesulfonamide (Example 20) was treated with 0.5 equivalents of fumaric acid and the resulting salt was crystallized from acetonitrile to give the rifled product, a compound of Formula I': mp 119°-122° C. Anal. Calc'd for $C_{22}H_{37}FN_2O_5S$: C, 57.36; H, 8.10; N, 6.08; S, 6.96. Found: C, 57.46; H, 8.16; N, 6.14; S, 6.98.

EXAMPLE 22

N-(4-(4-(Ethyl(3-cyclopropylpropyl)amino)1-hydroxybutyl)phenyl)methanesulfonamide Step I. A 60% mineral oil suspension of sodium hydride (5.34 g, 0.134 mol) was washed several times with hexane to remove the oil and dried with a stream of $N_2$. The solid was slurried in 14.5 mL of THF under $N_2$ and stirred with a motor stirrer. A solution of 10 g (0.116 mol) of 4-pentene-1-ol in 77.5 mL of THF as added dropwise over 30 min. After stirring for 45 min, a solution of 23.31 g (0.136 mol) of benzyl bromide in 96.8 mL of THF was added dropwise over 40 min. The mixture was stirred for 18 h and then mixed carefully with water. It was extracted with EtOAc. The extracts were washed several times with brine, dried ($MgSO_4$) and concentrated. The liquid was distilled under reduced pressure to give 8.46 g bp 60°-85° C. and 12.058 g bp 85°-88° C. of product: NMR ($CDCl_3$) δ1.72 (m, 2H), 2.15 (m, 2H), 3.48 (t, 2H), 4.50 (s, 2H), 4.97 (m, 2H), 5.81 (m, 1H), 7.34 (m, 5H); MS m/z (relative intensity) 176 ($M^+$, 9.0), 107 (12.7), 106 (14.3), 105 (18.2), 91 (100).

Step II. The method of Friedrich and Lewis[4] was used for this preparation. To a 3 neck flask filled with $N_2$ and equipped with a mechanical stirrer (off) was added in turn 2.97 g (45.4 mmol) of zinc dust, 0.45 g (4.54 mmol) of cuprous chloride, 4.3 mL of $Et_2O$, 0.91 mL (11.5 mmol) of diiodomethane and 0.065 mL (0.91 mmol) of acetyl chloride. The mechanical stirrer was turned on and the mixture immersed into an oil bath preheated to 45°. After 5 min there was added over 6.5 min a solution of 2.0 g (11.3 mmol) of the product from Step I in 1.5 mL of $Et_2O$. There was then added over 15 min a solution of 0.91 mL (11.3 mmol) of diiodomethane in 1.5 mL of $Et_2O$. After heating for 22 hrs the mixture was cooled to room temperature and transferred to an erlenmeyer flask with $Et_2O$. After cooling in an ice bath there was added dropwise 7 mL of saturated aqueous $NH_4Cl$. A suspended solid was collected on a filter and washed several times with pentane and then twice with saturated aqueous $NH_4Cl$. (Caution: Dispose of the solid wet—do not let it dry!) The aqueous layer from the combined filtrates was washed twice with pentane. The combined organic fractions were washed 3 times with 2N NaOH, once with brine, dried over $MgSO_4$ and concentrated in vacuo. The residue was chromatographed over silica gel (1.5% EtOAc:hexane) to yield 1.70 g of a mixture (NMR) of product and unreacted starting material.

A N$_2$ covered, dry ice:Me$_2$CO cooled solution of the above mixture plus 3.80 g of a mixture generated from another reaction in 227 mL of EtOAc was treated with ozone (bubbled in) for 17 min followed by 27 mL of dimethylsulfide, added over 1 min. The cold bath was removed and after stirring for 1.25 h at ambient temperature the reaction mixture was concentrated in vacuo. The residue was chromatographed over silica gel (1.5% EtOAc:hexane) to yield 3.513 g of product: NMR (CDCl$_3$) δ0.01 (m, 2H), 0.39 (m, 2H). 0.66 (m, 1H), 1.28 (m, 2H), 1.73 (m, 2H), 3.51 (t, 2H), 4.50 (s, 2H), 7.33 (m, 5H); MS m/z (relative intensity) 190 (M+, 0.3), 91 (100).

Step III. To a solution of 0.5 g (2.63 mmol) of the product from Step II in 5 mL of absolute EtOH was added ca. ⅛ teaspoon of Raney-nickel. After heating with good stirring in an oil bath at 80° for 4 h, the mixture was allowed to cool and the catalyst was collected on a filter and washed well with EtOH. The combined filtrates were concentrated in vacuo. The residue was treated with Et$_2$O and a small amount of flocculent material was removed by filtration through Celite. The filtrate was concentrated in vacuo. To a solution of the residue in 5 mL of absolute EtOH was added 0.1 g of 10% Pd/C catalyst. The mixture was placed on an atmospheric hydrogenator with good stirring. There was an uptake of 57.3 mL of H$_2$ over 25 min; after an additional 1 h the catalyst was removed by filtration over Celite and washed well with EtOH and CH$_2$Cl$_2$. The combined filtrates were concentrated in vacuo and the residue was chromatographed over silica gel (10% EtOAc:hexane) to yield 0.1215 g (46.1%) of product: NMR (CDCl$_3$) δ0.02 (m, 2H), 0.42 (m, 2H), 0.67 (m, 1H), 1.27 (m, 2H), 1.48 (s, 1H), 1.69 (m, 2H), 3.68 (m, 2H).

Step IV. To a N$_2$ covered solution of 0.597 g (5.96 mmol) of the product from Step III in 11 mL of benzene was added 1.72 g (6.55 mmol) of triphenylphosphine. After cooling in an ice bath there was added in portions over 25 min, 1.17 g (6.55 mmol) of N-bromosuccinimide. After stirring in the cold for 30 min and then at room temperature for 3.75 h the reaction mixture was poured into 40 mL of pentane. A suspended solid was collected on a filter and washed well with pentane. The combined filtrates were concentrated in vacuo. The residue was treated with pentane and additional solid was collected on a filter and washed with pentane. The combined filtrates were washed in turn with cold 5% aqueous sodium thiosulfate, 0.5N NaOH and brine, dried over MgSO$_4$ and concentrated in vacuo. After standing in the refrigerator for 17 h the residue was treated again with pentane and more solid was removed by filtration and washed with additional pentane. The combined filtrates were concentrated in vacuo to yield 0.3809 g (39.2%) of product 1-bromo-3-cyclopropylpropane: NMR (CDCl$_3$) δ0.06 (m, 2H), 0.43 (m, 2H), 0.66 (m, 1H), 1.35 (m, 2H), 1.98 (m, 2H), 3.47 (t, 2H).

Step V. According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react will 1-bromo-3-cyclopropylpropane (Step IV) to give the titled product, a compound of Formula I'. The high resolution FAB mass spectrum had (M+H)+ at m/z 369. Theory for C$_{19}$H$_{33}$N$_2$O$_3$S: 369.2212; measured: 369.2207.

EXAMPLE 23

N-(4-(4-(Ethyl(4-cyclopropylbutyl)amino)-1-hydroxybutyl)phenyl)methanesulfonamide Step I. To a N$_2$ covered solution of 5.7 g (56.9 mmol) of 5-hexen-1-ol in 115 mL of Et$_2$O was added 7.8 mL (85.0 mmol) of 3,4-dihydro-2H-pyran and 1.32 g (5.69 mmol) of camphorsulfonic acid. After stirring at room temperature for 3.5 h and then standing for 19 h the reaction mixture was washed 3 times with aqueous NaHCO$_3$, dried over MgSO$_4$ and concentrated in vacuo. The residue was distilled under reduced pressure to yield 11.42 g of product: bp 53°-55° (0.07 mmHg); NMR (CDCl$_3$) δ1.6 (m, 10H), 2.08 (m, 2H), 3.43 (m, 2H), 3.79 (m, 2H), 4.58 (m, 1H), 4.98 (m, 2H), 5.81 (m, 1H).

Step II. To a N$_2$ covered solution of 0.15 g (0.775 mmol) of cupric acetate monohydrate in 39 mL of glacial acetic acid warmed to 110° in an oil ball was added 2.71 g (41.5 mmol) of zinc dust. Vigorous gas evolution was observed and after stirring for 5 min the oil bath was removed and the stirrer was shut off allowing the solid to settle. The acetic acid was pipetted off and the solid was washed with an additional 39 mL of acetic acid. This second portion of acetic acid was pipetted off and the solid was then washed to neutrality will six 30 mL portions of Et$_2$O. To a suspension of the solid in 8 mL of Et$_2$O warmed to 50° in an oil bath was added several drops of diiodomellane followed by a mixture of 3.57 g (19.4 mmol) of the product from Step I and 2.18 mL (27.1 mmol) of diiodomethane, added over 27 min. After heating at 50° for 18 h the reaction mixture was diluted with Et$_2$O and the suspended solid was collected on a filter and washed well with Et$_2$O. The combined filtrates were concentrated in vacuo. The residue was chromatographed over silica gel (1.25% EtOAc:hexane) to yield 1.75 g of a mixture of the cyclopropane and starting olefin (detected using a silver nitrate impregnated silica gel TLC plate, eluting will 1.50% EtOAc-hexane). A solution of this mixture (1.75 g) and 1.4 g of a similar mixture obtained from other reactions in 130 mL of EtOAc was cooled in dry ice:Me$_2$CO and treated with O$_3$ (bubbled in) for 17 min. The O$_3$ was shut off and there was then added 15.6 mL of dimethylsulfide. The cold bath was removed and after stirring at room temperature for 1.75 h the mixture was concentrated in vacuo. The residue was chromatographed over silica gal (1.5% EtOAc:0.05% Et$_3$N:hexane) to yield 0.907 g of product:

NMR (CDCl$_3$) δ0.07 (m, 2H), 0.32 (m, 2H), 0.59 (m, 1H), 1.15 (m, 2H), 1.5 (m, 10H), 3.32 (m, 1H), 3.44 (m, 1H), 3.67 (m, 1H), 3.81 (m, 1H), 4.52 (m, 1H); MS m/z (relative intensity) 169 (1.8), 115 (1.3), 101 (2.5), 97 (6.0), 85 (100), 55 (27.2).

Step III. To a N$_2$ covered solution of 0.960 g (4.84 mmol) of the product from Step II in 125 mL of MeOH was added 0.20 g (0.87 mmol) of camphorsulfonic acid. After stirring at room temperature for 22.5 h the reaction mixture was concentrated in vacuo. A solution of the residue in EtOAc was washed 3 times with aqueous NaHCO$_3$, dried over MgSO$_4$ and concentrated in vacuo. The residue was chromatographed over silica gel (10% EtOAc:hexane) to yield 0.4199 g (76.0%) of the alcohol product: NMR (CDCl$_3$) δ0.01 (m, 2H), 0.40 (m, 2H), 0.66 (m, 1H), 1.24 (m, 2H), 1.46 (m, 2H), 1.60 (m, 2H), 1.83 (s, 1H), 3.65 (t, 2H).

Step IV. To a N$_2$ covered, ice bath cooled solution of 0.4199 g (3.68 mmol) of the product from Step III and 1.06 g (4.04 mmol) of triphenylphosphine in 7 mL of benzene was added 0.72 g (4.04 mmol) of N-bromosuccinimide in potions over 33 min. After stirring in the cold for 30 min and at room temperature for 4.5 h the reaction mixture was poured into 25 mL of pentane. After swirling occasionally for 10 min a suspended solid was collected on a filter and washed well with pentane. The combined filtrates were concentrated in vacuo and the residue was treated with pentane. Additional solid precipitated and was collected on a filter and washed with pentane. The combined filtrates were washed in turn with cold aqueous 5% sodium thiosulfate, 0.5N NaOH and brine, dried over MgSO$_4$ and concentrated in vacuo. The residue was chromatographed over silica gel (1% EtOAc:hexane) to yield 0.4183 g (64.2%) of the 1-bromo-4-cyclopropylbutane: NMR (CDCl$_3$) δ0.01 (m, 2H), 0.41 (m, 2H), 0.66 (m, 1H), 1.22 (m, 2H), 1.54 (m, 2H), 1.90 (m, 2H), 3.42 (t, 2H).

Step V. According to Procedure B (Example 17, Step IV), a stirred mixture of N-[4-[4-(ethylamino)-1-hydroxybutyl]phenyl]methanesulfonamide Example 7, Step II) and sodium bicarbonate in acetonitrile was allowed to react with 1-bromo-4-cyclopropylbutane (Step IV) to give the titled product, a compound of Formula I'. The high resolution mass spectrum had M$^+$ at m/z 382. Theory for C$_{20}$H$_{34}$N$_2$O$_3$S: 382.2290; measured: 382.2298.

EXAMPLE 24

N-(4-(4-(Ethyl(cyclohexylmethyl)amino-1-hydroxybutyl)phenylmethanesulfonamide

According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react with cyclohexylmethyl bromide to give the titled product, a communal of Formula I'. The high resolution mass spectrum had M$^+$ at m/z 382. Theory for C$_{20}$H$_{34}$N$_2$O$_3$S: 382.2290; measured: 382.2297.

EXAMPLE 25

N-(4-(4-(Ethyl(5 -acetoxy-5 -methylhexyl)amino)-1-hydroxybutyl)phenyl)methanesulfonamide Step I. A stirred solution of 4-chloro-1-butanol (23.0 mL, 0.230 mol) and 3,4-dihydro-2H-pyran (32.0 mL, 0.351 mol) in Et$_2$O (500 mL) was treated with 10-camphorsulfonic acid (5.33 g, 0.023 mol) and kept, under nitrogen, at ambient temperature for 18 h. Additional 3,4-dihydro-2H-pyran (5 mL, 0.0548 mol) was added and the reaction was allowed to continue for 5 h. The mixture was then washed thoroughly with 8% NaHCO$_3$ and then water and brine. It was dried (MgSO$_4$) and concentrated. The residue was distilled to give the product: bp 58° C. (0.07 to 0.1 mm Hg).

Step II. A mechanically stirred mixture of magnesium turnings (1.27 g, 0.052 mol) and THF (5 mL) was warmed to reflux and treated dropwise with a solution of the product from Step I (5.00 g, 0.260 mol) in THF (27 mL). After a small amount had been added the reaction was started by the addition of several drops of 1,2-dibromoethane and crushing some of the magnesium. After the addition the mixture was refluxed for 1 h, cooled in an ice bath and treated dropwise with a solution of acetone (2.29 mL, 0.0312 mol) in THF (24 mL). This mixture was kept at ambient temperature for 20 h, cooled in an ice bath and treated, dropwise with saturated NH$_4$Cl (29.5 mL). It was stirred for 1 h and then extracted with EtOAc. The extracts were washed with dilute aqueous NaCl, dried (MgSO$_4$) and concentrated. The residue was chromatographed over silica gel with 5 to 20% EtOAc-0.05% Et$_3$N-hexane to give 1.64 g (29.2%) of product: NMR (CDCl$_3$) δ1.22 (s, 6H), 1.58 (m, 13H), 3.47 (m, 2H), 3.82 (m, 2H), 4.58 (m, 1H); MS m/z (relative intensity) 115 (18.7), 101 (15.3), 85 (100), 59 (25.3); IR (film) 3452 cm$^{-1}$.

A column fraction (0.46 g) that contained a small amount of impurity was also obtained.

Step III. A mixture of the product from Step II (1.67 g, 7.72 mmol), triethylamine (2.15 mL, 0.0154 mol), acetic anhydride (1.46 mL, 0.0154 mol) and 4-dimethylaminopyridine (0.094 g, 0.77 mmol) was stirred, under nitrogen, for 18 h, diluted with hexane and washed with 2N HCl until acidic. It was then washed with water, saturated NaHCO$_3$ and brine and concentrated. The residue was chromatographed over silica gel with 10% EtOAc-0.05% Et$_3$N-hexane to give 1.62 g (81.2%) of product: NMR (CDCl$_3$) δ1.43 (s, 6H), 1.61 (m, 12H), 1.97 (s, 3H), 3.45 (m, 2H), 3.8 (m, 2H), 4.58 (m, 1H); FAB MS m/z (relative intensity) 259 (M+H$^+$, 3.5), 199 (2.5), 175 (2.0), 115 (7.6), 101 (8.4), 85 (100).

Step IV. A stirred solution of the product from Step III (1.6 g, 6.19 mmol) in absolute EtOH (50 mL) was treated with pyridinium p-toluenesulfonate (0.203 g, 0.808 mmol) and kept under nitrogen at ambient temperature for 70 h. It was then concentrated. A solution of the residue in EtOAc was washed with saturated NaHCO$_3$ and brine, dried (MgSO$_4$) and concentrated. The residue was chromatographed on silica gel with 10–30% EtOAc-0.05% Et$_3$N-hexane to give 0.873 g (80.9%) of product: NMR (CDCl$_3$) δ1.43 (s, 6H), 1.58 (m, 6H), 1.99 (s, 3H), 2.13 (s, 1H), 3.65 (t, 2H); MS m/z (relative intensity) 114 (21.8).

Step V. A stirred mixture of the product from Step IV (0.873 g, 5.00 mmol) and triphenylphosphine (1.45 g, 5.50 mmol) in benzene (9 mL), under nitrogen, was cooled in an ice bath and treated portionwise, during 15 min with N-bromosuccinimide (0.980 g, 5.5 mmol). It was kept in the ice bath for 30 min and at ambient temperature for 5 h. The mixture was then diluted with pentane (20 mL) and :filtered. The filtrate was concentrated and the residue was mixed with Et$_2$O; the solution was washed with cold 5% sodium thiosulfate, 0.5N NaOH and brine, dried (Na$_2$SO$_4$) and concentrated to give; 1.08 g (91.1%) of 5-acetoxy-1-bromo-5-methylhexane: NMR (CDCl$_3$) δ1.43 (s, 6H), 1.49 (m, 2H), 1.82 (m, 4H), 1.98 (s, 3H), 3.43 (t, 2H); MS m/z (relative intensity) 176 (9.4).

Step VI. According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react with 5-acetoxy-1-bromo-5-methylhexane (Step V) to give the titled product, a compound of Formula I'. The mass spectrum had M$^+$ at m/z 442.

EXAMPLE 26

N-[4-[4-[Ethyl(5-hydroxy-5 -methylhexyl)amino]-1-hydroxybutyl]phenyl]methanesulfonamide A stirred mixture of the product from Example 25 (0.92 g, 2.08 mmol) and 17.2 mL of a solution of potassium carbonate (5 g) in MeOH (80 mL) and water (20 mL) was refluxed, under nitrogen for 24 h. An additional 17.2 mL of the potassium carbonate solution was added and reflux was continued for 24 h. The mixture was then concentrated to remove MeOH and the aqueous residue was adjusted to pH 8 and washed with EtOAc. The aqueous solution was then concentrated to dryness, and the solid residue was extracted with $CH_2Cl_2$. This extract was concentrated and the residue was chromatographed on silica gel with 10% MeOH—1% $NH_4OH$-$CHCl_3$ to give 0.292 g (35.1%) of the titled product, a compound of Formula I': NMR ($CDCl_3$) δ1.09 (t, 3H), 1.21 (s, 6H), 1.53 (m, 9H), 1.97 (m, 1H), 2.55 (m, 6H), 2.94 (s, 3H), 4.61 (m, 1H), 7.15 (d, 2H), 7.35 (d, 2H); MS m/z (relative intensity) 400 ($M^+$, 17.4), 385 (14.5), 367 (11.1), 321 (36.6), 299 (92.8), 172 (100).

EXAMPLE 27

N-(4-(4-(Ethyl(5-fluoro-5-methylhexyl)amino)-1-hydroxybutyl)phenyl)methanesulfonamide Step I. A stirred solution of diethylaminosulfur trifluoride (DAST) (1.95 mL, 0.0148 mol) in $CH_2Cl_2$ (4.8 mL) was cooled, under nitrogen, in a dry ice-acetone bath and treated, dropwise during 5 min, with a solution of the product from Example 25, Step II (1.60 g, 7.40 mmol) in $CH_2Cl_2$ (4.8 mL). The mixture was kept in the dry ice bath for 15 min and in an ice bath for 10 min. It was then transferred with a pipette to 24.2 mL of a stirred 10% aqueous $Na_2CO_3$ solution. The resulting mixture was extracted with $CH_2Cl_2$. The extracts were washed with water, dried ($MgSO_4$) and concentrated. The residue was chromatographed over silica gel with 2.5% EtOAc-0.05% $Et_3N$-hexane to give 1.22 g (75.6%) of product: NMR ($CDCl_3$) δ1.31 (s, 3H), 1.38 (s, 3H), 1.6 (m, 12H), 3.47 (m, 2H), 3.82 (m, 2H), 4.58 (m, 1H).

Step II. A stirred solution of the product from Step I (1.22 g, 5.59 mmol) in MeOH (144 mL) was treated with camphorsulfonic acid (0.233 g, 1 mmol) and kept at ambient temperature, under nitrogen for 20 h. It was then concentrated and the residue was mixed with EtOAc (100 mL) and thoroughly washed with saturated $NaHCO_3$. The EtOAc solution was dried ($MgSO_4$) and concentrated. The residue was chromatographed on silica gel with 5-30% EtOAc-hexane to give 0.400 g (53.4%) of product: NMR ($CDCl_3$) δ1.31 (s, 3H), 1.36 (s, 3H), 1.58 (m, 6H), 2.72 (s, 1H), 3.64 (t, 2H).

Step III A stirred solution of the product from Step II (0.400 g, 2.98 mmol) and triphenylphosphine (0.859 g, 3.28 mmol) in benzene (5.4 mL) was cooled in an ice bath and treated, portionwise during 20 min, with N-bromosuccinimide (0.580 g, 3.28 mmol). The mixture was kept in the ice bath for 30 min and at ambient temperature for 5 h. It was then diluted with pentane (20 mL) and cooled in an ice bath. The solid was collected by filtration and washed with pentane. The filtrate was concentrated and the residue was mixed with pentane, cooled in an ice bath and filtered. The filtrate was concentrated and the residue was mixed with $Et_2O$; the $Et_2O$ solution was washed with cold 5% sodium thiosulfate, 0.5N NaOH and brine, dried ($MgSO_4$) and concentrated to give 0.51 g (86.8%) of 1-bromo-5-fluoro-5-methylhexane.

Step IV. According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react with 1-bromo-5-fluoro-5-methylhexane (Step III) to give the titled product, a compound of Formula I'. The high resolution mass spectrum had $M^+$ at m/z 402. Theory for $C_{20}H_{35}FN_2O_3S$: 402.2352; measured: 402.2350.

EXAMPLE 28

N-[4-[4-[Ethyl(3-cyclopentylpropyl)amino)-1-hydroxybutyl)phenyl]methanesulfonamide Step I. The product from Example 7, Step II was condensed with 3-cyclopentylpropionic acid according to Procedure E (Example 7, Step III). The product was recrystallized from EtOAc-hexane to give N-[4-[4-[(2-Cyclopentylethylcarbonyl)ethylamino]-1-hydroxybutyl]phenyl]methanesulfonamide (42.8%): mp 101°-102° C.; NMR ($CDCl_3$) δ1.13 (m, 5H), 1.63 (m, 13H), 2.3 (m, 2H), 2.99 (d, 3H), 3.39 (m, 4H), 4.72 (m, 1H), 7.07 (s, 1H), 7.24 (m, 4H); MS m/z (relative intensity) 410 ($M^+$, 2.8), 392 (3.2), 331 (11.5), 223 (29.0), 207 (6.3), 200 (2.9), 189 (19.4); IR (Nujol) 3397, 3190, 1591 $cm^{-1}$. Anal. calc'd for $C_{21}H_{34}N_2O_4S$: C, 61.43; H, 8.35; N, 6.82; S, 7.81. Found: C, 61.21; H, 8.56; N, 6.59; S, 7.77.

Step II. According to Procedure C (Example 7, Step IV), N-[4-[4-[(2-cyclopentylethylcarbonyl)ethylamino]-1-hydroxybutyl]phenyl]methanesulfonamide (Step I) was reduced with lithium aluminum hydride to give the titled product, a compound of Formula I'. The high resolution FAB mass spectrum had $(M+H)^+$ at m/z 397. Theory for $C_{21}H_{37}N_2O_3S$: 397.2525; measured: 397.2533.

EXAMPLE 29

N-(4-(4-(Ethyl(7,7-difluoroheptyl)amino)-1-hydroxybutyl)phenyl)methanesulfonamide, (E)-2-Butenedioate (2:1 salt)

Step I. A solution of 8-bromo-1-octene (5.0 g, 0.026 mol) in 25 mL of MeOH and 5 mL of $CH_2Cl_2$ was cooled to −40° C. and treated with $O_3$ while the mixture was cooled to −50 to −60° C. After 30 min the mixture turned bluish and after another 10 min of $O_3$ treatment the mixture was purged with a stream of $N_2$ for 5 min. With the mixture still at −50° C. and covered with a blanket of $N_2$, 2.5 mL of dimethylsulfide was added. This mixture was stirred for 1 h at −40° C., 1 h at −20° C. and then allowed to warm to −10° C. over 1 h. A vacuum from the water aspiration was applied to remove some of the excess dimethylsulfide, and the residue concentrated further on a rotary evaporator (house vacuum). The residue was treated with 10 mL of water and this mixture was extracted with hexane; the organic extracts were washed with water, then brine, dried ($MgSO_4$) and concentrated. A portion of the crude product (0.7 g) was chromatographed under pressure to give 7-bromoheptaldehyde: NMR ($CDCl_3$) δ1.41 (m, 4H), 1.63 (m, 2H), 1.87 (m, 2H), 2.45 (m, 2H), 3.41 (m, 2H), 9.78 (s, 1H).

Step II. A solution of 7-bromoheptaldehyde, the product from Step I, (0.74 g, 3.8 mmol) in 1 mL of $CCl_4$ was cooled in an ice bath under a stream of $N_2$ and treated with DAST (1 mL, 7.6 mmol); an immediate yellow color appeared. The flask was stoppered with a teflon stopper and a plastic clip; the mixture was stirred in the cold for 75 min and at ambient temperature for 48 h. It was then diluted with hexane and mixed with ice. The layers were separated and the organic solution was washed sequentially with water, 10% Na$_2$CO$_3$ (aqueous), water and brine; dried (MgSO$_4$) and concentrated to give 0.54 g of crude material. This was combined with 0.15 g of crude material from a previous run and chromatographed under pressure, over 200 mL of silica gel (230–400 mesh) with 3.5% CH$_2$Cl$_2$/hexane to give 0.3 g of product 1-bromo-7,7-difluoroheptane: NMR (CDCl$_3$) δ1.47 (m, 6H), 1.84 (m, 4H), 3.41 (t, 2H), 5.61, 5.80, 5.99 (t's, 1H).

Step III. According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react with 1-bromo-7,7-difluoroheptane (Step II) to give N-[4-[4-[ethyl(7,7-difuoroheptyl)amino]-1-hydroxybutyl]phenyl]methanesulfonamide, a compound of Formula I'. A mixture of this compound and 0.5 equivalents of fumaric acid was crystallized from acetone to give the titled product, mp 147°–148° C. Anal. calc'd for C$_{22}$H$_{36}$F$_2$N$_2$O$_5$S: C, 55.21; H, 7.58; N, 5.85; S, 6.70. Found: C, 54.98; H, 7.50; n, 5.77; S, 6.55.

EXAMPLE 30

N-(4-(4-(Ethyl(6,6-difluorohexyl)amino)-1-hydroxybutyl)phenyl)methanesulfonamide, (E)-2-Butenedioate (2:1 salt)

Step I. A stirred solution of oxalyl chloride (6.7 mL, 77 mmol) in 50 mL of CH$_2$Cl$_2$, under nitrogen, was cooled to −70° C. and treated dropwise over 15 min with 10.9 mL (154 mmol) of DMSO in 50 mL of CH$_2$Cl$_2$. The mixture was stirred for 20 min at −70° C. and was then treated over 7 min with 6-bromohexanol (6.8 g, 37.6 mmol) in 50 mL of CH$_2$Cl$_2$. The mixture was stirred as the cold bath was allowed to warm to −20° C. over 2¼ h. After 1¼ h at −20° to −25° C. the bath was taken to −65° C. and the reaction mixture was treated dropwise over 5 min with 32.1 mL of Et$_3$N. This mixture was stirred for 30 min after the cold bath had been removed. This mixture was transferred to a separatory funnel and diluted to ca. 350 mL with CH$_2$Cl$_2$. The organic mixture was washed with water then with brine, dried (MgSO$_4$) and concentrated in vacuo. The residue was taken up in hexane and this solution was washed with water; the aqueous washes were extracted with additional hexane and the organic extracts were washed with brine, dried (MgSO$_4$) and concentrated in vacuo to give 6.38 g (95%) of 6-bromohexanol: NMR (CDCl$_3$) δ1.42 (m, 2H), 1.58 (m, 2H), 1.82 (m, 2H), 2.41 (m, 2H), 3.35 (t, 2H), 9.71 (s, 1H).

Step II. A stirred solution of the product from Step I (1.0 g, 5.58 mmol) in 1.5 mL of CCl$_4$, under a stream of N$_2$, was cooled in an ice bath and treated with 1.5 mL (1.8 g, 11.2 mmol) of DAST via pipette. The reaction flask was sealed with a teflon stopper and the stopper secured with a plastic clip. The mixture was stirred in the cold for 90 min and at room temperature overnight to give an amber fluid with a dark oil therein. This mixture was taken up in a pipette and added dropwise, with swirling, to 20 mL of ice/water; solid Na$_2$CO$_3$ was then added to a pH of 7. The aqueous mixture was extracted with hexane; the extracts were washed with water then with brine, dried (MgSO$_4$) and concentrated. The residue was chromatographed under pressure, over 300 mL of silica gel with 2.5% CH$_2$Cl$_2$/hexane to give 0.37 g (33%) of product 1-bromo-6,6-difluorohexane: NMR (CDCl$_3$) δ1.50 (m, 4H), 1.89 (m, 4H), 3.42 (t, 2H), 5.63, 5.82, 6.00 (t's, 1H).

Step III. According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react with 1-bromo-6,6-difluorohexane (Step II) to give N-[4-[4-[ethyl(6,6-difluorohexyl)amino]-1-hydroxybutyl]phenyl]methanesulfonamide, a compound of Formula I'. A mixture of this compound and 0.5 equivalents of fumaric acid was crystallized from acetone to give the titled product, mp 88°–90° C. Anal. calc'd for C$_{21}$H$_{34}$F$_2$N$_2$O$_5$S: C, 54.29; H, 7.38; N, 6.03; S, 6.90. Found: C, 54.42; H, 7.58; N, 5.74; S, 6.58.

EXAMPLE 31

N-(4-(4-(Ethyl(5-cyclopropylpentyl)amino)-1-hydroxybutyl)phenylmethanesulfonamide, (E)-2-Butenedioate (2:1 salt)

Step I. A stirred solution of methyltriphenylphosphonium bromide (2.33 g, 6.5 mmol) in 15 mL of Et$_2$O was cooled in an ice bath, under nitrogen, and treated in portions over 1 min with potassium tert-butoxide (0.7 g, 6.24 mmol). The mixture was stirred in the cold for 1 h. A solution of the product from Example 30, Step I, 6-bromohexanol (1.12 g, 6.26 mmol) in 5 mL of Et$_2$O was added over 3 min to the cold reaction mixture which was then allowed to warm to room temperature over 4 h. This mixture was diluted with Et$_2$O and quenched with water. The layers were separated and the aqueous layer was extracted with Et$_2$O; the extracts were washed with water, then with brine, dried (MgSO$_4$) and concentrated on a rotary evaporator at room temperature. The residue was extracted with hexane, the hexane extracts were pooled and adsorbed on a column of 300 g of silica gel (230–400 mesh). The column was eluted under pressure, with hexane to give 0.42 g (38%) of 7-bromo-1-heptenyl which was stored over 3 Å molecular sieves: NMR (CDCl$_3$) δ1.43 (m, 4H), 1.87 (m, 2H), 2.06 (m, 2H), 3.41 (t, 2H), 4.98 (m, 2H), 5.80 (m, 1H).

Step II. Zinc dust (40 g) was mixed with 10% HCl (15 mL) to give a thick sludge. This was mixed with water (15 mL) and filtered. The solid was washed with water (30 mL) and then twice with acetone (10 mL) and dried under reduced pressure. A mixture of this material (3.0 g) and CuCl (0.45 g, 4.5 mmol) under nitrogen was warmed with a heat gun. After cooling, without stirring, this mixture was treated with 8 mL of ether, 0.91 mL (10.3 mmol) of diiodomethane and 0.066 mL (0.93 mmol) of acetyl chloride; the reaction flask was immersed in an oil bath preheated to 47° C. and the stirrer was started. After 2–3 min a brisk reaction ensued; the Zn turned from grey to black. After a total of 5 min the product from Step I (2.0 g, 11.3 mmol) in 3 mL of Et$_2$O was added dropwise over 10 min. Another 0.91 mL (10.3 mmol) of diiodomethane in 3 mL of ether was added over 20 min in several portions, dropwise. The mixture was stirred at 47°–49° C. (bath temp.) for 4.5 h and allowed to cool. It was transferred to a beaker with Et$_2$O; this mixture was treated with 10 mL of saturated aqueous NH$_4$Cl. The aqueous layer was drawn off and extracted twice more with Et$_2$O. The organic extracts were washed with saturated aqueous NH$_4$Cl; the organic layers were pooled, dried (MgSO$_4$) and concentrated to give 2.0 g of a yellow oil. This material was shown to contain approximately 25% product and 75% starting alkene. This was resubjected to the same reaction conditions and work-up to give a crude product that was chromatographed, under pressure, over 700 mL of silica gel (230–400 mesh) with 0.5% CH$_2$Cl$_2$/hexane to give 0.83 g (30.8%) of 1-cyclopropyl-5-iodopentane: NMR (CDCl$_3$) δ0.00 (m, 2H), 0.40 (m, 2H), 0.65 (m, 1H), 1.27 (m, 2H), 1.42 (m, 4H), 1.83 (m, 2H), 3.20 (t, 2H); MS m/z (relative intensity) 238 (M+0.69), 210 (1.4), 196 (4.3), 155 (4.0), 127 (1.7), 111 (7.8), 83 (13.2), 69 (100), 55 (89.8), 40 (56.5).

Step III. According to Procedure B (Example 17, Step IV), a stirred mixture of N-[4-[4-(ethylamino)-1-hydroxybutyl]phenyl]methanesulfonamide (Example 7, Step II) and sodium bicarbonate in acetonitrile was allowed to react with 1-cyclopropyl-5-iodopentane (Step II) to give N-[4-[4-[ethyl(5-cyclopropylpentyl)amino]-1-hydroxybutyl]phenyl]methanesulfonamide, a compound of Formula I'. A mixture of this compound and 0.5 equivalents of fumaric acid was crystallized from acetone to give the titled product, mp 127°–128° C. Anal. calc'd for C$_{23}$H$_{38}$N$_2$O$_5$S: C, 60.76; H, 8.42; N, 6.16; S, 7.05. Found: C, 60.66; H, 8.30; N, 6.17; S, 7.04.

EXAMPLE 32

N-(4-(4-(Ethyl(7-fluoroheptyl)amino)-1-hydroxybutyl)-phenyl)methanesulfonamide, (E)-2-Butenedioate (2:1 salt)

Step I. A solution of 8-bromo-1-octene (5.0 g, 26 mmol) in a mixture of 25 mL of MeOH and 5 mL of CH$_2$Cl$_2$ was cooled to −50° C. and treated with O$_3$ until a blue color persisted (45 min) and then for an additional 10 min. The mixture, at −40° C., was purged with N$_2$ for 10 min, allowed to warm to −20° C., under N$_2$, and kept at −20° C. while 1.3 g (34 mmol) of sodium borohydride was added in portions over 30 min (evolution of H$_2$ was evident at each addition). The mixture was stirred 30 min more at −20° C. and quenched with the dropwise addition of 20 mL of H$_2$O. This mixture was stirred for 10 min, and extracted with hexane; the organic extracts were washed with water, then brine, dried (Na$_2$SO$_4$) and concentrated to give 3.65 g (72%) of 7-bromo-1-heptanol: NMR (CDCl$_3$) δ1.44 (m, 9H), 1.85 (m, 2H), 3.41 (t, 2H), 3.65 (t, 2H).

Step II. A stirred solution of 7-bromo-1-heptanol, the product of Step I, (1.53 g, 7.85 mmol) in 2.5 mL of CCl$_4$ was cooled in an ice bath, under nitrogen, and treated with 2.25 mL (17.0 mmol) of DAST; the flask was stoppered with a teflon stopper and secured with a plastic clip. The mixture was stirred in the cold 30 min and, after removing the ice bath, at ambient temperature. After 4.5 h an aliquot was assayed by TLC to show unreacted starting material; 0.7 mL (5.3 mmol) more of the DAST was added, the flask stoppered and stirred at room temperature overnight. The resultant mixture was added dropwise to 25 mL of ice/water over 5 min and this was extracted with hexane. The organic extracts were washed sequentially with water, 10% aqueous Na$_2$CO$_3$, and brine. The pooled extract was dried (MgSO$_4$) and concentrated. The residue was chromatographed under pressure over 300 mL of silica gel (230–400 mesh) with 4% CH$_2$Cl$_2$/hexane to give 0.9 g (53%) of product, 1-bromo-7-fluoroheptane: NMR (CDCl$_3$) δ1.43 (m, 6H), 1.71 (m, 2H), 1.87 (m, 2H), 3.42 (t, 2H), 4.37, 4.52 (t's, 2H).

Step III. According to Procedure B (Example 17, Step IV) a stirred mixture of N-[4-[4-(ethylamino)-1-hydroxybutyl]phenyl]methanesulfonamide (Example 7, Step II) and sodium bicarbonate in acetonitrile was allowed to react with 1-bromo-7-fluoroheptane (Step II) to give N-[4-[4-[ethyl(7-fluoroheptyl)amino]-1-hydroxybutyl]-phenyl]methanesulfonamide, a compound of Formula I'. A mixture of this compound and 0.5 equivalents of fumaric acid was crystallized from acetone to give the titled product, mp 137°–138° C. Anal. calc'd for C$_{22}$H$_{37}$N$_2$O$_5$S: C, 57.36; H, 8.10; N, 6.08; S, 6.96. Found: C, 57.34; H, 8.08; N, 6.03; S, 6.95.

We claim:

1. A compound which is:
   a) N-(4-(4-(Ethyl(6-acetoxy-6-methylheptyl)amino)-1-hydroxybutyl)phenyl)methanesulfonamide;
   b) N-(4-(4-(Ethyl(6-fluoro-6-methylheptyl)amino)-1-hydroxybutyl)phenyl)methanesulfonamide.
   c) N-[4-[4-[(6,6-Difuoroheptyl)ethylamino]-1-hydroxybutyl]phenyl]methanesulfonamide;
   d) N-[4-[4-[(6-Fluoroheptyl)ethylamino]-1-hydroxybutyl]phenyl]methanesulfonamide;
   e) N-(4-(4-((6-Fluoroheptyl)ethylamino)-1-hydroxybutyl)phenyl)methanesulfonamide, (E)-2-butenedioate (2:1 salt);
   f) N-(4-(4-(Ethyl(3-cyclopropylpropyl)amino)1-hydroxybutyl)phenyl)methanesulfonamide;
   g) N-(4-(4-(Ethyl(4-cyclopropylbutyl)amino)-1-hydroxybutyl)phenyl)methanesulfonamide;
   h) N-(4-(4-(Ethyl(cyclohexylmethyl)amino-1-hydroxybutyl)phenyl)methanesulfonamide;
   i) N-[4-[4-[Ethyl(5-hydroxy-5-methylhexyl)amino]-1-hydroxybutyl]phenyl]methanesulfonamide;
   j) N-(4-(4-(Ethyl(5-fluoro-5-methylhexyl)amino)-1-hydroxybutyl)phenyl)methanesulfonamide;
   k) N-(4-(4-(Ethyl(7,7-difluoroheptyl)amino)-1-hydroxybutyl)phenyl)methanesulfonamide, (E)-2-Butenedioate (2:1 salt);
   l) N-(4-(4-(Ethyl(6,6-difluorohexyl)amino)-1-hydroxybutyl)phenyl)methanesulfonamide, (E)-2-Butenedioate (2:1 salt);
   m) N-(4-(4-(Ethyl(5-cyclopropylpentyl)amino)-1-hydroxybutyl)phenyl)methanesulfonamide, (E)-2-Butenedioate (2:1 salt);
   n) N-(4-(4-(Ethyl(7-fluoroheptyl)amino)-1-hydroxybutylphenyl)methanesulfonamide, (E)-2-Butenedioate (2:1 salt) or (other) pharmacologically acceptable salts thereof.

2. A method for treating cardiac arrhythmia in patients by administering a therapeutically effective amount of a compound of claim 1 or (other) pharmacologically acceptable salts thereof.

3. The method of claim 2 where said effective amount is from about 0.01 to about 300 mg.

4. The method of claim 2 where said compound is in a unit dosage form for oral, sublingual, transdermal or parenteral administration.

* * * * *